United States Patent [19]
Thome et al.

[11] Patent Number: 5,861,021
[45] Date of Patent: Jan. 19, 1999

[54] MICROWAVE THERMAL THERAPY OF CARDIAC TISSUE

[76] Inventors: Scott P. Thome, 535 Aberdeen Dr., Waite Park, Minn. 56387; Eric N. Rudie, 8519 Walnut Grove La. North, Maple Grove, Minn. 56387; Mitchell Dann, Star Rte. Box 3668, Jackson, Wyo. 83001; Teruo T. Hirose, 5830 Tyndall Ave., Bronx, N.Y. 10471

[21] Appl. No.: 771,214

[22] Filed: Dec. 20, 1996

Related U.S. Application Data

[62] Division of Ser. No. 664,363, Jun. 17, 1996, abandoned.

[51] Int. Cl.⁶ ..................................................... A61N 5/02
[52] U.S. Cl. ........................ 607/101; 607/102; 607/105; 607/113; 607/156
[58] Field of Search ................................ 604/96–98, 114, 604/264, 280; 607/101–105, 113, 116, 154, 156

[56] References Cited

U.S. PATENT DOCUMENTS

| | | |
|---|---|---|
| 2,407,690 | 9/1946 | Southworth . |
| 2,642,874 | 6/1953 | Keeling . |
| 2,813,531 | 11/1957 | Lee . |
| 3,125,096 | 3/1964 | Antiles et al. . |
| 3,228,400 | 1/1966 | Armao . |

(List continued on next page.)

FOREIGN PATENT DOCUMENTS

| | | |
|---|---|---|
| 0 048 402 | 9/1981 | European Pat. Off. . |
| 0 105 677 | 9/1983 | European Pat. Off. . |
| 0 246 176 | 5/1987 | European Pat. Off. . |
| 0 248 758 | 5/1987 | European Pat. Off. . |
| 0 253 677 | 7/1987 | European Pat. Off. . |
| 0 335 022 | 3/1988 | European Pat. Off. . |
| 0 370 890 | 11/1989 | European Pat. Off. . |
| 0 459 535 A2 | 11/1989 | European Pat. Off. . |
| 0 462 302 A1 | 6/1990 | European Pat. Off. . |
| 0 449 472 A1 | 3/1991 | European Pat. Off. . |
| 0 519 958 B1 | 3/1991 | European Pat. Off. . |
| 0 485 323 A1 | 11/1991 | European Pat. Off. . |
| 0 629 382 A1 | 8/1993 | European Pat. Off. . |
| 0 628 288 A2 | 5/1994 | European Pat. Off. . |

(List continued on next page.)

OTHER PUBLICATIONS

Valdagni, Amichetti: *Clinical Hyperthermia: Five Year's Experience,* Strahlentherapie und Onkologie 163 (1987), 443–445.

Anghileri et al., *Hyperthermia in Cancer Treatment,* vol. III, 1986 by CRC Press, Inc.

Astrahan et la., *Thermometry Characteristics of the BSD Interstitial Hyperthermia Applicator,* Endocurietherapy/Hyperthermia Oncology, Jul. 1987. vol. 2, pp. 153–160.

*International Journal of Hyperthermia,* vol. 5, No. 1, pp. 37–51, Jan.–Feb. 1989.

(List continued on next page.)

*Primary Examiner*—Michael Peffley
*Assistant Examiner*—Stephen Huang

[57] ABSTRACT

A method of applying microwave energy to cardiac tissue uses a catheter adapted for insertion into a cardiac chamber and which includes a microwave antenna, a cooling lumen structure, and an inflatable cooling balloon. Necrosing levels of microwave energy are delivered from the microwave antenna to diseased cardiac tissue spaced from the catheter. Tissues immediately surrounding the catheter are cooled and microwave energy emitted by the antenna is selectively absorbed by the cooling lumen structure surrounding the antenna. The cooling balloon of the catheter is positioned adjacent the antenna and partially surrounds the cooling lumen structure on one side of the catheter to provide additional cooling capability and additional microwave energy absorption on the side of the catheter opposite the diseased cardiac tissue to prevent unwanted heating of blood within the cardiac chamber.

20 Claims, 7 Drawing Sheets

U.S. PATENT DOCUMENTS

| | | |
|---|---|---|
| 4,140,130 | 2/1979 | Storm, III . |
| 4,148,005 | 4/1979 | Larsen et al. . |
| 4,154,246 | 5/1979 | LeVeen . |
| 4,162,500 | 7/1979 | Jacobi et al. . |
| 4,204,549 | 5/1980 | Paglione . |
| 4,253,469 | 3/1981 | Aslan . |
| 4,285,346 | 8/1981 | Armitage . |
| 4,290,435 | 9/1981 | Waggott . |
| 4,311,154 | 1/1982 | Sterzer et al. . |
| 4,312,364 | 1/1982 | Convert et al. . |
| 4,375,220 | 3/1983 | Matvias . |
| 4,448,198 | 5/1984 | Turner . |
| 4,497,324 | 2/1985 | Sullivant et al. . |
| 4,557,272 | 12/1985 | Carr . |
| 4,583,556 | 4/1986 | Hines et al. . |
| 4,601,296 | 7/1986 | Yerushalmi . |
| 4,612,940 | 9/1986 | Kasevich et al. . |
| 4,632,127 | 12/1986 | Sterzer . |
| 4,643,186 | 2/1987 | Rosen et al. . |
| 4,662,383 | 5/1987 | Sogawa et al. . |
| 4,669,475 | 6/1987 | Turner . |
| 4,672,963 | 6/1987 | Barken . |
| 4,676,258 | 6/1987 | Inokuchi et al. . |
| 4,681,122 | 7/1987 | Winters et al. . |
| 4,690,156 | 9/1987 | Kikuchi et al. . |
| 4,700,716 | 10/1987 | Kasevich et al. . |
| 4,708,718 | 11/1987 | Daniels . |
| 4,709,698 | 12/1987 | Johnston et al. . |
| 4,712,559 | 12/1987 | Turner . |
| 4,776,086 | 10/1988 | Kasevich et al. . |
| 4,777,951 | 10/1988 | Cribier et al. . |
| 4,798,215 | 1/1989 | Turner . |
| 4,800,899 | 1/1989 | Elliott . |
| 4,808,164 | 2/1989 | Hess . |
| 4,813,429 | 3/1989 | Eshel et al. . |
| 4,823,812 | 4/1989 | Eshel et al. . |
| 4,825,880 | 5/1989 | Stauffer et al. . |
| 4,832,023 | 5/1989 | Murphy-Chutorian et al. . |
| 4,841,988 | 6/1989 | Fetter et al. . |
| 4,860,752 | 8/1989 | Turner . |
| 4,865,047 | 9/1989 | Chou et al. . |
| 4,878,492 | 11/1989 | Sinofsky et al. . |
| 4,907,589 | 3/1990 | Cosman . |
| 4,924,863 | 5/1990 | Sterzer . |
| 4,927,413 | 5/1990 | Hess . |
| 4,932,420 | 6/1990 | Goldstolm . |
| 4,945,318 | 7/1990 | Kabachinski et al. . |
| 4,946,449 | 8/1990 | Davis, Jr. . |
| 4,955,377 | 9/1990 | Lennox et al. . |
| 4,961,738 | 10/1990 | Mackin . |
| 4,967,765 | 11/1990 | Turner et al. . |
| 4,993,430 | 2/1991 | Shimoyama et al. . |
| 4,994,014 | 2/1991 | Gordon . |
| 4,998,933 | 3/1991 | Eggers et al. . |
| 5,003,991 | 4/1991 | Takayama et al. . |
| 5,007,437 | 4/1991 | Sterzer . |
| 5,026,959 | 6/1991 | Ito et al. . |
| 5,045,056 | 9/1991 | Behl . |
| 5,056,531 | 10/1991 | Shimoyama . |
| 5,057,106 | 10/1991 | Kasevich et al. . |
| 5,097,845 | 3/1992 | Fetter et al. . |
| 5,106,360 | 4/1992 | Ishiwara et al. . |
| 5,151,100 | 9/1992 | Abele et al. . |
| 5,234,004 | 8/1993 | Hascoet et al. . |
| 5,312,392 | 5/1994 | Hofstetter et al. . |
| 5,323,781 | 6/1994 | Ideker et al. ............................ 607/122 |
| 5,344,398 | 9/1994 | Hara . |
| 5,344,435 | 9/1994 | Turner et al. . |
| 5,364,392 | 11/1994 | Warner et al. . |
| 5,370,676 | 12/1994 | Sozanski et al. . |
| 5,370,678 | 12/1994 | Edwards et al. . |
| 5,464,437 | 11/1995 | Reid et al. ............................... 607/101 |
| 5,470,352 | 11/1995 | Rappaport ............................... 607/156 |
| 5,509,929 | 4/1996 | Hascoet et al. ......................... 607/101 |
| 5,545,137 | 8/1996 | Rudie et al. ............................. 607/101 |
| 5,628,770 | 5/1997 | Thome et al. ........................... 607/101 |

FOREIGN PATENT DOCUMENTS

| | | |
|---|---|---|
| 58-70219 | 11/1981 | Japan . |
| 60-263164 | 11/1985 | Japan . |
| 63-177867 | 1/1987 | Japan . |
| 1266548 A1 | of 0000 | U.S.S.R. . |
| 1 238 200 | 11/1968 | United Kingdom . |
| WO 81/03616 | 6/1981 | WIPO . |
| WO 86-91919 | 9/1985 | WIPO . |
| WO 89/05609 | 12/1988 | WIPO . |
| WO 89/11311 | 5/1989 | WIPO . |
| WO 91/11975 | 2/1991 | WIPO . |
| WO 91/13650 | 3/1991 | WIPO . |
| WO 94/02204 | 7/1993 | WIPO . |
| WO 94/22384 | 3/1994 | WIPO . |
| WO 94/26178 | 5/1994 | WIPO . |
| WO 94/26186 | 5/1994 | WIPO . |
| WO 94/26187 | 5/1994 | WIPO . |
| WO 94/26188 | 5/1994 | WIPO . |

OTHER PUBLICATIONS

Astrahan et al., *Microwave Applicator for Transurethral Hyperthermia of Benign Prostatic Hyperplasia,* Int. J. Hyperthermia, 1989, vol. 5, No. 3, pp. 283–296.

Astrahan et al., *Interstitial Temperature Measurements During Transurethral Microwave Hyperthermia,* The Journal of Urology, vol. 145, pp. 304–308, Feb. 1991.

Astrahan et al., *Heating Characteristics of a Helical Microwave Applicator for Transurethral Hyperthermia of Benign Prostatic Hyperplasia,* Int. J. Hyperthermia, 1991, vol. 7, No. 1, pp. 141–155.

Baert, et al., *Treatment Response with Transurethral Microwave Hyperthermia in Different Forms of Benign Prostatic Hyperplasia: A Preliminary Report,* The Prostate 18:315–320 (1991), Wiley–Liss, Inc. 1991.

Baert, et al., *Transurethral Microwave Hyperthermia for Benign Prostatic Hyperplasia: Preliminary Clinical and Pathological Results,* The Journal of Urology, vol. 144, Dec., pp. 1383–1387, 1990.

M.L. Blute, et al., *Transurethral Microwave Thermotherapy for Prostatism: Early Mayo Foundation Experience,* Mayo Clinic Proceedings, vol. 67, pp. 417–495, May 1992.

Carter et al., *Single–Session Transurethral Microwave Thermotherapy for the Treatment of Benign Prostatic Obstruction,* Journal of Endourology, vol. 5 No. 2, 1991.

Cavaliere et al., *Selective Heat Sensitivity of Cancer Cells,* Cancer, Sep. 1967, vol. 20, pp. 1351–1381.

T.C. Cetas et al., *Thermometry consideration in localized hyperthermia,* Med. Phys. 5(2), Mar./Apr. 1978.

R.T. Constable et al., *Perturbation of the temperature distribution in microwave irradiated tissue due to the presence of metallic thermometers,* Med. Phys. 14(3), May/Jun. 1987.

Debicki et al., *Superficial and Intraurethral Applicators for Microwave Hyperthermia,* Consensus on Hypertherma for the 1990s, pp. 321–326. 1990.

Devonec et al., *The Effects of Transurethral Microwave Thermotherapy (T.U.M.T.) in Patients with Benign Prostatic Hypertrophy,* Eur Urol 1990, vol. 18, No. 1, p. 265.

Devonec et al., *Transurethral Microwave Heating of the Prostate—Or from Hyperthermia to Thermotherapy,* Journal of Endourology, Vol. 5, No. 2, pp. 129–135, 1991.

Marian et al., *Long Term Results of Transurethral Microwave Therapy (TUMT) in Patients with Benign Prostatic Hypertrophy*, The Journal of Urology, AUA Eighty–Sixth Annual Meeting, Jun. 2–6, 1991.

Devonec et al. *Clinical Response to Transurethral Microwave Thermotherapy is Thermal Dose Dependent*, Eur Urol. 1993, vol. 23, pp. 267–274.

Fajardo, *Pathological Effects of Hyperthermia in Normal Tissues*, Can Res Suppl 1984, vol. 44, pp. 4826s–4835s.

Field, *Hyperthermia in the Treatment of Cancer*, 1985 Douglas Lea Memorial Lecture, 1987 IOP Publishing Ltd.

Giovanella et al., *Selective Lethal Effect of Supranormal Temperatures on Human Neoplastic Cells*, Cancer Research Vol. 36, 3944–3950, Nov. 1876.

Harada, *The Application of Microwave Surgical Treatment to Urological Diseases: A Fundamental Examination about a Phantom and Thermal Distrubtion*, pp. 2173–2179.

Harada et al., *Hyperthermic Treatment with Intravesical Microwave Radiation for Bladder Cancer*, 1984.

Harada et al., *Microwave Surgical Treatment of Diseases of Prostate*, Urol, Dec. 1985, vol. 26, No. 6, pp. 572–576.

Harada et al., *Transcystoscopic Intracavitary Irradiation for Carcinoma of the Bladder: Technique and Preliminary Results*, Urol. Oct. 1987, vol. 138, No. 4, pp. 771–775.

Harada et al., *Microwave Surgical Treatment of the Prostate: Clinical Application of Microwave Surgery as a Tool for Improved Prostatic Electrosection*, Urol Int 1987, vol. 42, pp. 127–131.

Harada et al., *Ultrasonography for Prostatic Microwave Coagulation*, Urol Radiol 1990, vol. 12, pp. 46–49.

James e tal., *The Effect of Insertion Depth on the Theoretical SAR Patterns of 915 MHz Dipole Antenna Arrays for Hyperthermia*, Int J. Hyperthermia 1989, vol. 5, No. 6, pp. 733–747.

Kaver et al., *The Effect of Hyperthermia on Human Prostatic Carcinoma Cell Lines: Evaluation in Vitro*, J Urol 1989, vol. 141, pp. 1025–1027.

Larson et al., *Accurate Prostatic Thermal Mapping in 11 Patietns Treated with the Urologix T3 System: Understanding the Decay of Temperatures*, 11th World Congress on Endourology, Abstract, Oct. 20–23, 1993.

Lee et al., *Interstitial Microwave Applicators*, Int J. Rad Oncol Biol Phys 1986, vol. 12, pp. 2003–2008.

Leib et al., *Histopathological Observations in the Canine Prostate Treated by Local Microwave Hyperthermia*, Prostate 1986, vol. 8, pp. 93–102.

Leybovich et al., *Intracavitary Hyperthermia: A Newly Designed Applicator for Tracheal Tumors*, Endourcurietherapy–Hyperthermia Oncology 1987, vol. 3, pp. 23–29.

Li, Ding–Jui et al., *Design and Thermometry of an Intracavitary Microwave Applicator Suitable for Treatment of Some Vaginal and Rectal Cancers*, J. Radiation Oncology Biol. Phys., vol. 10, pp. 2155–2162, 1984.

Linder et al., *Local Hyperthermia of the Prostate Gland for the Treatment of Benign Prostatic Hypertrophy and Urinary Retention*, Br J. Urol 1987, vol. 60, pp. 567–571.

Abstracts, J. Urol, Apr. 1989, vol. 141, p. 355A.

Linder et al., *Local Hyperthermia of the Prostate Gland for the Treatment of Benign Prostatic Hypertrophy and Urinary Retention*, Br J Urol 1990, vol. 65, pp. 201–203.

Linder et al., *Serum Prostate Specific Antigen Levels During Hyperthermia Treatment of Benign Prostatic Hyperplasia*, J. Urol 1990, vol. 144, pp. 1388–1389.

Linder et al., *Complications in Hyperthermia Treatment of Benign Prostatic Hyperplasia*, J Urol 1990, vol. 144, pp. 1390–1392.

Magin, R. L. et al., *Thermal Destruction of the Canine Prostate by High Intensity Microwaves*, Journal of Surgical Resarch 29, 265–275 (1980).

Manning et al., *Clincial Hyperthermia: Results of a Phase I Trial Employing Hyperthermia Alone or on Combination with External Beam or Interstitial Radiotherapy*, Cancer 1982, vol. 49, pp. 05–216.

Marmor, *Interactions of Hyperthermia and Chemotherapy in Animals*, Cancer Research 1979, vol. 39, pp. 2269–2276.

Marmor et al., *Combined Radiation and Hyperthermia in Superficial Human Tumors*, Cancer 1980, vol. 46, pp. 1986–1991.

Abstracts, Fourteenth Annual Meeting of the American Society of Clinical Oncology 1978, vol. 19, p. 330.

McNeal, *The Prostate Gland: Morphology ad Pathobiology*, Monographs in Urology 1988, pp. 36–54.

Mendecki et al., *Microwave Applicators for Localized Hyperthermia Treatment of Malignant Tumors*, J. Bioengineering 1977, vol. 1, pp. 511–518.

Mendecki et al., *Microwave Applicators for Localized Hyperthermia Treatement of Cancer of the Prostate*, Int J Radiation Oncology Biol Phys 1978, vol. 4, pp. 1095–1103.

Neumann, H. A. et al., *VIIth Meeting of the European Society for Hyperthermic Oncology (ESHO)*, Paris, Sep. 16–18, 1985 pp. 523, 557 (Nr.9).

Overgaard, *Effect of Hyperthermia on Malignant Cells in Vivo; A Review and Hypothesis*, Cancer 1977, vol. 39, pp. 2637–2646.

Overgaard, *Fractionated Radiation and Hyperthermia: Experimental and Clinical Studies*, Cancer 1981, vol. 48, pp. 1116–1123.

Rigatti et al., *Local Microwave Hyperthermia and Benign Prostatic Hyperplasia Induced Bladder Outlet Obstruction*, Book: Consensus on Hyperthermia for the 1990's, 1990, pp. 433–437.

Roehrborn et al., *Temperature Mapping in the Canine Prostate During Transurethrally–Applied Local Microwave Hyperthermia*, The Prostate 1992, vol. 20, pp. 97–104.

Salles–Cunha et al., *Steady Magnetic Fields in Noninvasive Electromagnetic Flowmetry*, Proceedings of the IEEE, vol. 68, No. 1, Jan. 1980.

Samulski e tal., *Temperature Measurements in High Thermal Gradients: II. Analysis of Conduction Effects*, Int J. Radiation Oncology Biol Phys 1985, vol. 11, pp. 963–971.

Sapozink et al., *Introduction to Hyperthermia Device Evaluation*, Int. J. Hyperthermia, 1988, vol. 4, No. 1, pp. 1–15.

Sapozink et al., *Transurethral Hyperthermia for Benign Prostatic Hyperplasia: Preliminary Clinical Results*, Journal of Urology, May 1990, vol. 143, pp. 944–950.

Saranga et al., *Local Microwave Hyperthermia in the Treatment of Benign Prostatic Hypertrophy*, British Journal of Urology, 1990, vol. 65, pp. 349–353.

Sathiaseelan et al., *A Clinical Microwave Hyperthermia System with Multipoint Sealtime Thermal Dosimetry*, British Journal Radiology. 1985, vol. 58, pp. 1187–1195.

Satoh et al., *Implantable Helical Coil Microwave Antenna for Interstitial Hyperthermia*, Int. J. Hyperthermia, 1988, vol. 4, No. 5, pp. 497–512.

Scheiblich et al., *Radiofrequency–Induced Hyperthermia in the Prostrate*, Journal of Microwave Power, pp. 472–478.

Servadio et al., *Further Observations on the Use of Local Hyperthermia for the Treatment of Diseases of the Prostate in Man,* Ur. Urol. 1986, vol. 12, pp. 38–40.

Servadio et al., *Local Thermotherapy of the Benign Prostate: A 1–Year Follow–Up,* Eur Urol 1990, vol. 18, pp. 169–173.

Servadio et al., *Chronic Abacterial Prostatitis and Hyperthermia: A Possible New Treatment?,* British Journal of Urology, 1991, vol. 67, pp. 308–311.

Song, *Effect of Hyperthermia on Vascular Functions of Normal Tissues and Experimental Tumors: Brief Communication,* J. Natl. Cancer Inst., vol. 60, No. 3, Mar. 1978.

Marberger et al., *Other Non–Medical Therapies (Excluding Lasers) in the Treatment of BPH,* pp. 453–466.

Watson, *Heat and the Prostate,* Inst. of Urol, 1993, vol. 23 (suppl 1), pp. 60–62.

de la Rosette et al., *Clinical Results with Microwave Thermotherapy of Benign Prostatic Hyperplasia,* Eur Urol 1993, vol. 23 (suppl 1), pp. 68–71.

Sugaar et al., *A Histopathologic Study on the Effects of Radiofrequency Thermotherapy on Malignant Tumors of the Lung,* American Cancer Society, 1979, vol. 43, pp. 767–783.

Trembly, *The Effects of Driving Frequency and Antenna Length on Power Deposition Within a Microwave Antenna Array Used for Hyperthermia,* IEEE Transactions on Biomedical Engineering, vol. BME–32, No. 2, Feb. 1985.

Tucker et al., *The In Vivo Effect of Regional Hyperthermia on Dunning R3327 Prostatic Tumor,* The Prostate, vol. 18, pp. 321–329, (1991).

Turner, *Recent Developments and Work in Progress,* Strahlentherapie und Onkologie, vol. 163 (1987), pp. 422–424.

Watson, et al., *Performance Charateristics of a Helical Microwave Interstitial Antenna for Local Hyperthermia,* Med. Phys., vol. 14, No. 2, Mar./Apr. 1987, pp. 235–237.

Xu et al., *Transurethral Thermal Therapy (T3) for the Treatment of Benign Prostatic Hyperplasia (BPH) in the Canine: Analysis Using Pennes Bioheat Equation,* Adv. in Bioheat and Mass Transfer 1993 ASME Winter Annual Meeting, HTD–vol. 268, pp. 31–35.

Yerushalmi et al., *Normal Tissue Response to Localized Deep Microwave Hyperthermia in the Rabbit's Prostate: A preclinical Study,* Int. J. Radiation Oncology Biol Phys 1982, vol. 9, pp. 77–82.

Yerushalmi et al., *Local Hyperthermia for Treatment of Carcinoma of the Prostate: A Preliminary Report,* The Prostate, vol. 3, pp. 623–630, 1982.

Yerushalmi et al., *Localized Deep Microwave Hyperthermia in the Treatment of Poor Operative Risk Patients with Benign Prostatic Hyperplasia,* The Journal of Urology, Vol. 133, May 1985, pp. 873–876.

Yerushalmi, *Localized Deep Microwave Hyperthermia (LDMWH) for BPH: Comparison of Short & Long Term Results,* The Journal of Urology, Apr. 1987, p. 358A.

Yerushalmi, *Use of Local Hyperthermia for the Treatment of Benign Prosatic Hyperplasia,* Concensus on Hyperthermia for the 1990s, pp. 167–176.

*Interstitial EM Applicator/Temperature Probes,* by Paul F. Turner, 1980.

*Transurethral Hyperthermia for Benign Prostatic Hyperplasia: Preliminary Clinical Results,* by Michael D. Sapozink et al.

*Short and Long Term Histological Effects of Transurethral Microwave Therapy (TUMT) on Benign Prostatic Hypertrophy,* by Devonec et al.

*A Comparison of Transurethral and Transrectal Microwve Hyperthermia in Poor Surgical Risk Benign Prostatic Hyperplasia Patients,* by B. Stawarz et al.

*Interluminal Hyperthermia for Esphageal Tumors,* by Matsuda et al.

Thirty–Seventh Annual Meeting of the Radiation Research Society, Ninth Annual Meeting of the North American Hyperthermia Group, Mar. 18–23, 1989.

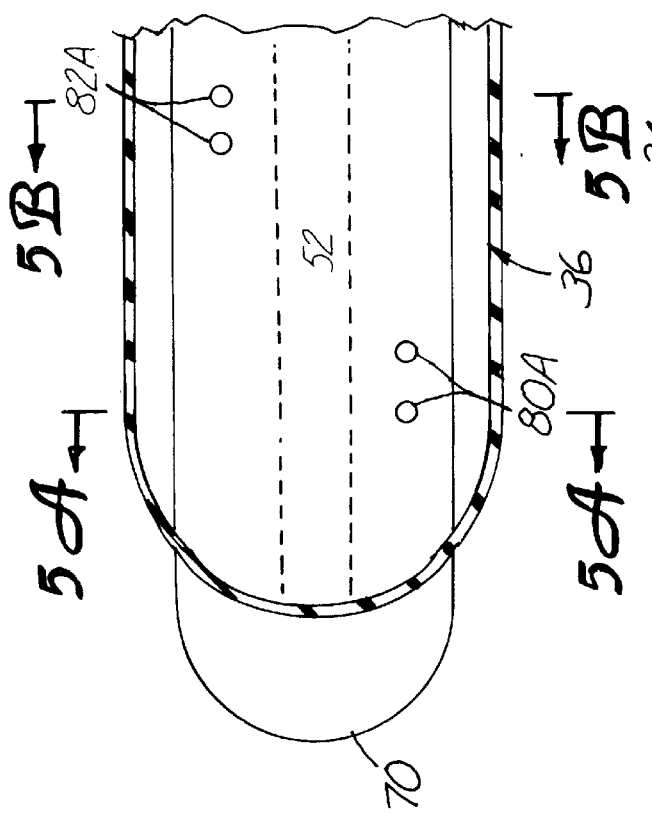
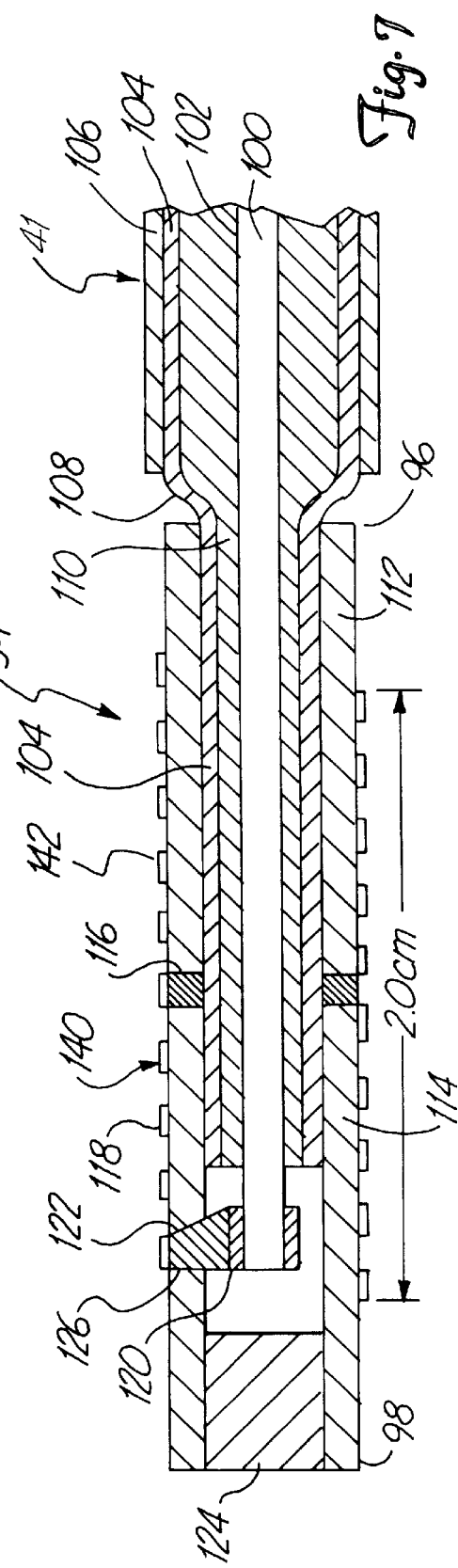

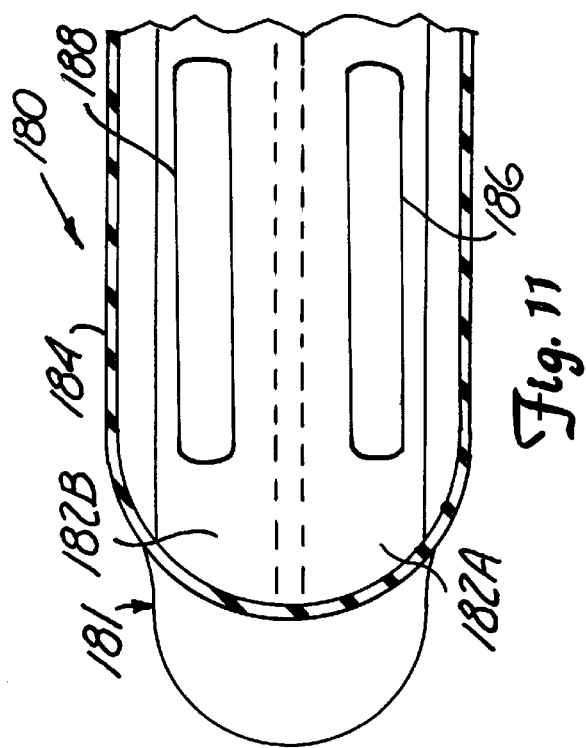
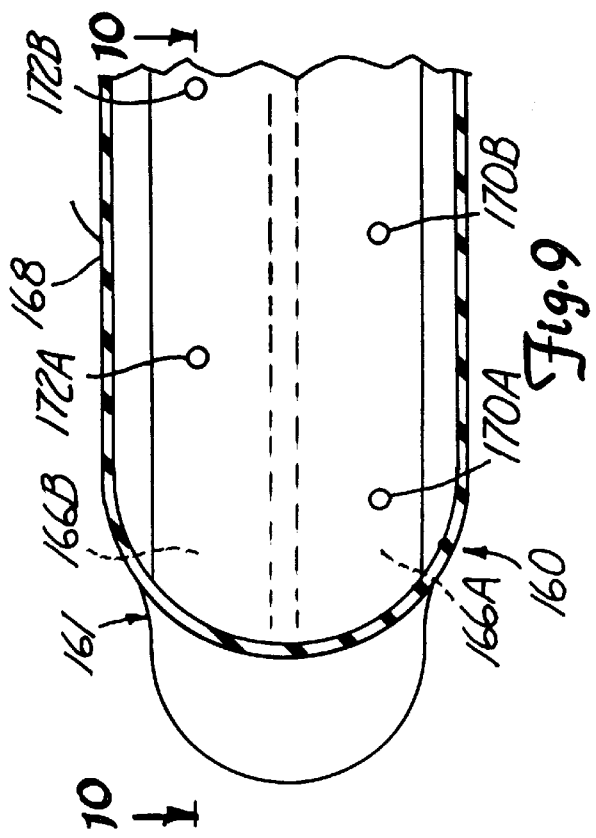
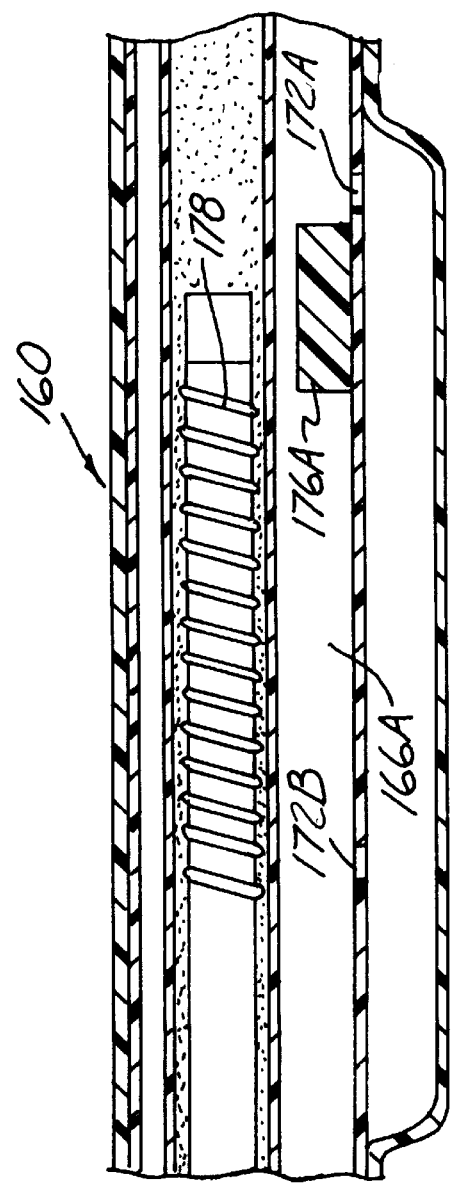

MICROWAVE THERMAL THERAPY OF CARDIAC TISSUE

REFERENCE TO CO-PENDING APPLICATIONS

The present application is a divisional of, and claims priority under 35 U.S.C. § 120, from application Ser. No. 08/664,363, filed Jun. 17, 1996, titled ARTERIAL MICROWAVE APPLICATOR WITH COOLING (now abandoned).

Reference is also hereby made to application Ser. No. 08/672,504, filed Jun. 17, 1996, titled DEVICE FOR TRANSURETHRAL THERMAL THERAPY WITH COOLING BALLOON now U.S. Pat. No. 5,800,486, and application Ser. No. 08/672,505, filed Jun. 17, 1996, titled MICROWAVE ANTENNA FOR MICROWAVE APPLICATOR now U.S. Pat. No. 5,776,176.

BACKGROUND OF THE INVENTION

The present invention relates to the field of microwave thermal ablation therapy of tissue. In particular, the present invention relates to a catheter for microwave thermal ablation therapy of cardiac tissue to treat cardiac arrhythmias.

Cardiac arrhythmias are one type of irregular beating of the heart which can result from damage caused to a portion of cardiac tissue. Specifically, cardiac arrhythmias result when damaged cardiac tissue (e.g., along a ventricle or atrial wall) prevents the proper conduction of an electrical and rhythmic impulse through the ventricle wall or atrial wall in the region of damaged tissue. This disruption of the electrical and rhythmical impulse inhibits the chambers of the heart from contracting and expanding with the proper timing and the proper force.

Cardiac arrhythmias have traditionally been treated with medication and/or through surgery. However, medications are limited in their application since they are successful in treating only certain types of cardiac arrhythmias. On the other hand, while a portion of cardiac tissue which is damaged can be surgically removed, surgery carries much more risk than medicinal treatment of cardiac arrhythmias.

Alternative methods of treating cardiac arrhythmias include applying heat to the damaged cardiac tissue by inserting a catheter into a chamber of the heart, e.g., ventricle, and using the catheter to apply heat locally to ablate the damaged portion of cardiac tissue to neutralize its effect on the electrical and rhythmical impulse. For example, Fram PCT International Publication WO 94/07446, published Apr. 14, 1994, discloses a catheter and method for ablating electrically conductive pathways of a heart. This catheter includes a balloon mounted on a catheter shaft and a heating device located within the balloon to heat the fluid inside the balloon. The heated fluid heats the cardiac tissue by thermal conduction from the balloon fluid to the tissue through a wall of the balloon. This technique carries several disadvantages. First, since this method uses thermal conduction, the surface of the cardiac tissue immediately adjacent the outer surface of the balloon is necessarily heated yet cardiac tissue deep below the surface, where lesions are frequently located, remains unheated. Second, since the catheter necessarily heats the surface of the cardiac tissue, any healthy tissue on the surface of a wall of the cardiac chamber is unnecessarily damaged. Finally, this method of applying heat to cardiac tissue unnecessarily heats blood in the cardiac chamber (e.g., ventricle) surrounding a side of the catheter opposite a wall of the chamber. This technique can coagulate small portions of blood that pass through the particular chamber of the heart adjacent the catheter, thereby producing clotting and emboli in the bloodstream.

Other catheters ablate cardiac tissue using radio frequency or microwave energy that is transmitted from a distal end of the catheter through cardiac tissue to the site to be treated. Langberg U.S. Pat. No. 4,945,912 discloses a catheter including a microwave antenna for directing microwave energy to ablate cardiac tissue than is possible with conventional thermal conduction methods such as those disclosed in the Fram PCT Publication. However, these catheters also unnecessarily necrose healthy tissue immediately adjacent an outer surface of the catheter.

In an attempt to limit heating of tissue immediately adjacent a heat generating portion of a catheter, some cardiac ablation catheters include cooling systems incorporated into the catheter adjacent the heat generating portion of the catheter. Nardella, U.S. Pat. No. 5,334,193, discloses an ablation catheter which includes at its distal end, an electrode for directing radio frequency energy (RF) to necrose damaged cardiac tissue and a cooling lumen centrally aligned throughout the catheter for delivering cooling fluid adjacent the electrode for limiting heat transferred by the electrodes to adjacent tissues.

Other methods of protecting healthy tissue from the heat generated by an electrode of a microwave ablation catheter include attempts to selectively block the propagation of the microwave field generated by the electrode. Stern et al., U.S. Pat. No. 5,314,466, discloses a microwave ablation catheter including a structure for blocking the propagation of a microwave field in a desired direction to prevent undesired heating of blood within the cardiac chamber which surrounds the heat producing end of the catheter. This catheter also has a mechanism for pivoting a distal portion of its catheter relative to a remaining proximal portion of the catheter to orient the microwave field in a desired orientation relative to the tissue site to be treated.

Previous cardiac ablation catheters have attempted to limit the heat applied to tissues and/or blood immediately surrounding the heat producing end of the catheter. However, thus far, previous catheters have failed to: (1) deliver adequate microwave energy in cardiac tissue at depths which actually necrose the damaged tissue; (2) adequately cool healthy tissue immediately adjacent the microwave energy producing portion of the catheter; and (3) adequately protect a cardiac environment, such as blood, immediately surrounding an outer surface of the microwave energy producing portion of the catheter.

SUMMARY OF THE INVENTION

A method of the present invention applies microwave energy to cardiac tissue, while cooling the surface of the cardiac tissue. A catheter used in the method of the present invention preferably includes a microwave antenna, a cooling lumen structure, and an inflatable cooling balloon. The microwave antenna delivers necrosing levels of microwave energy to diseased cardiac tissue spaced from the catheter. The cooling lumen structure surrounds the antenna and cools tissues immediately adjacent the catheter. The cooling balloon is positioned adjacent the antenna and partially surrounds the cooling lumen structure on one side of the catheter to provide cooling capability and microwave energy absorption on the side of the catheter opposite the cardiac tissue. For example, the catheter can be positioned within a cardiac chamber of the heart (e.g. ventricle) so that a side of the catheter having the cooling balloon is disposed between the microwave antenna and blood flowing within the cardiac chamber. The cooling balloon acts to prevent the coagulation of blood in the chamber during the application of microwave energy to cardiac tissues adjacent an opposite side of the catheter. By adding additional cooling on one side of the catheter with a cooling balloon in the method of the present invention, greater necrosing temperatures can be applied in cardiac tissues at greater depths adjacent an opposite side of the catheter to ablate target cardiac tissue without harming blood and surrounding healthy tissues.

BRIEF DESCRIPTION OF THE DRAWINGS

FIG. 6 is a plan view of a second side of the catheter shaft shown in FIGS. 5A and 5B with a balloon portion removed and as taken along lines 6—6.

FIG. 7 is an enlarged sectional view of a microwave antenna incorporated into a catheter of the present invention.

FIG. 9 is a plan view of an alternate embodiment of second side of the catheter shown in FIG. 6.

FIG. 10 is a sectional view of FIG. 9 as taken along lines 10—10.

FIG. 11 is a plan view of an second alternate embodiment of second side of the catheter shown in FIG. 6.

DETAILED DESCRIPTION OF THE PREFERRED EMBODIMENTS

Figure 1:
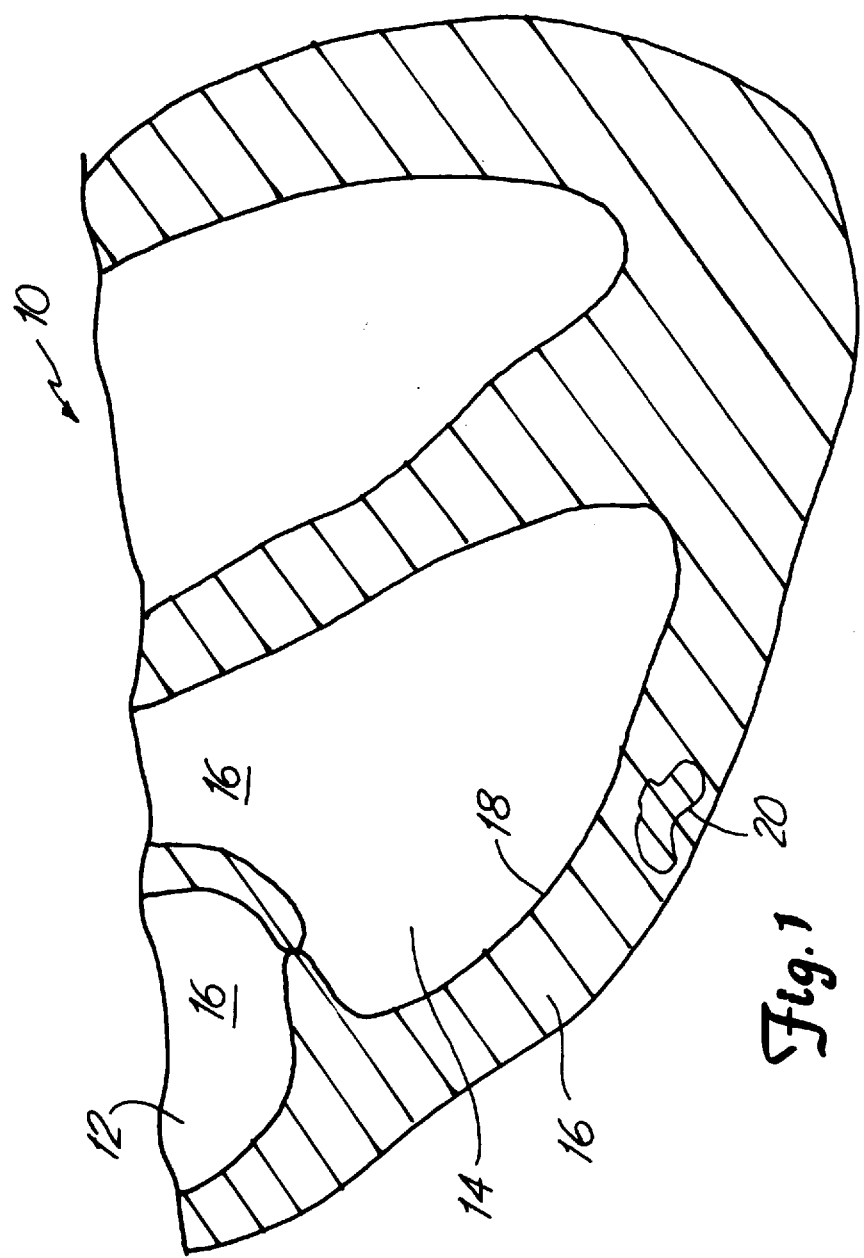
FIG. 1 is a sectional view of a ventricle of a human heart showing a portion of damaged cardiac tissue.

FIG. 1 is a vertical sectional view of a human heart showing a location of damaged tissue which can cause cardiac arrhythmia. Heart 10 includes right atrium 12, right ventricle 14, and blood 15 within atrium 12 and ventricle 14. Ventricle 14 includes wall 16, surface 18, and damaged tissue 20. The damaged tissue 20 of ventricle wall 16 which causes cardiac arrhythmias, such as ventricular tachycardia, can be effectively removed by heating and necrosing damaged tissue 20. Ideally, with the present invention, only damaged tissue 20 of ventricle wall 16 spaced from surface 18 is heated and necrosed while, at the same time, damage to ventricle wall surface 18 and to blood 15 is prevented. A selective thermal heating of damaged tissue 20 of ventricle wall 16 is made possible by microwave antenna-containing catheter 28 of the present invention, which is shown in FIG. 2.

Figure 2:
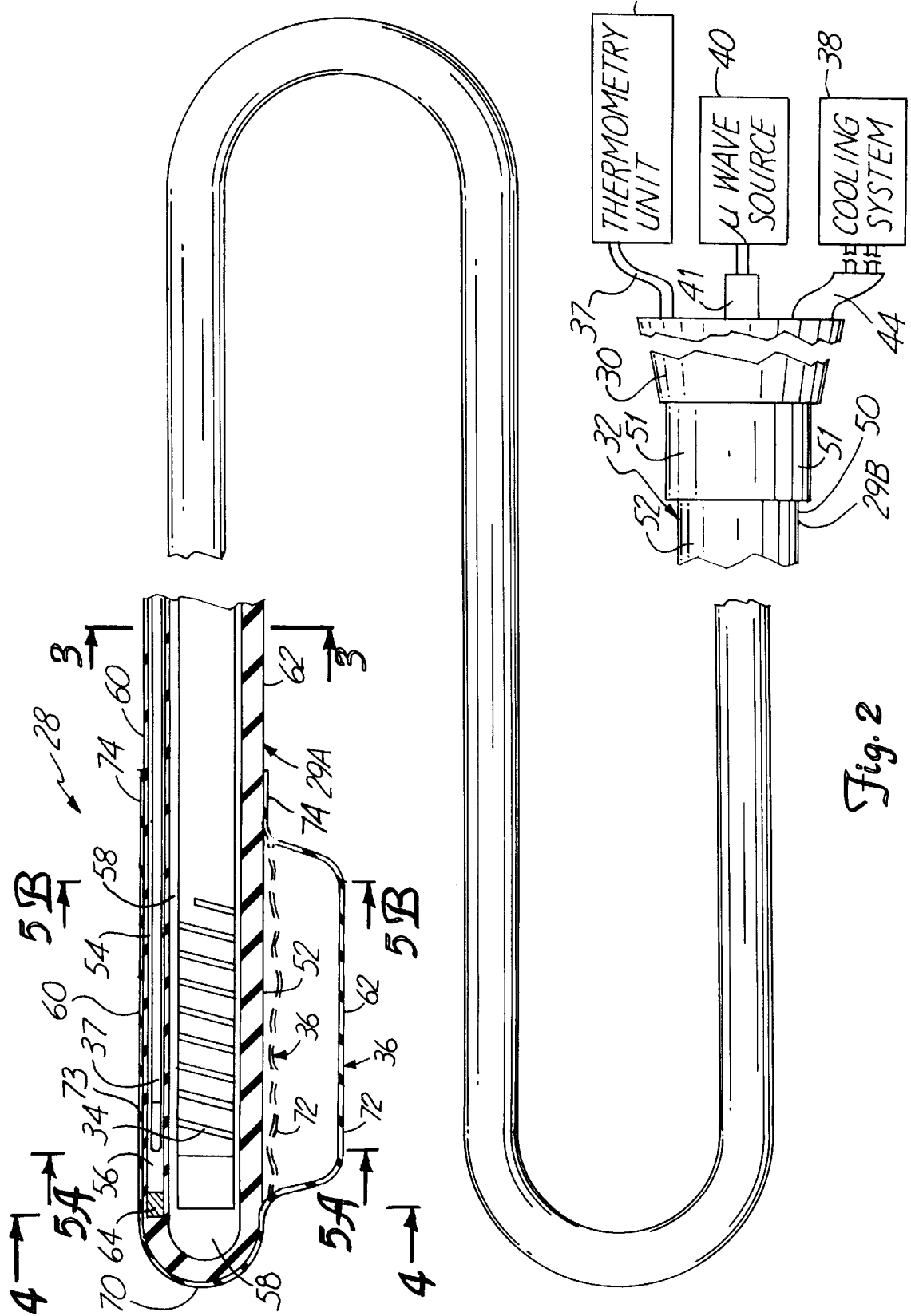
FIG. 2 is a sectional view of an intravascular ablation catheter of the present invention with a proximal end and a distal end of the catheter enlarged for clarity.

FIG. 2 shows a side view of catheter 28 including a sectional view of a distal end 29A of catheter 28 and a plan view of a proximal end 29B of catheter 28. Both distal end 29A and proximal end 29B are enlarged relative to shaft 32 of catheter 28 for illustrative purposes. As shown in FIG. 2, catheter 28 generally includes manifold 30, multi-lumen shaft 32, microwave antenna 34, cooling balloon 36, and thermometry sensor 37. Catheter 28 is used with cooling system 38, microwave generating source 40, and thermometry unit 42.

Manifold 30 receives coaxial cable 41 (from microwave generating source 40), thermometry sensor 37, and cooling system delivery tubing 44 for alignment with corresponding lumens within shaft 32. Shaft 32 is an extruded multi-lumen, intravascular catheter shaft connected to manifold 30 at proximal shaft end 50 via strain relief member 51.

Manifold 30 and shaft 32 are preferably made of a polymeric material such as polyethylene terephthalate (PET) sold by ATOCHEM, INC. (Glen Rock, N.J.) under the trademark PEBAX® or sold by Consolidated Polymers, Inc. under the tradename C-FLEX. The polymeric material preferably has a hardness of about 20 to about 80 on the Shore D hardness scale.

Shaft 32 also includes outer surface 52. In one preferred embodiment, shaft 32 includes a coating (e.g., TEFLON®) having a low coefficient of friction well known in the art forming outer surface 52 of shaft 32 to facilitate its advancement through a guide catheter positioned within the vascular system. Shaft 32 has an outer diameter of about 0.1 inches, suitable for insertion within a 10 French size guide catheter. Shaft 32 is long enough (e.g., 135 centimeters) and of a small enough diameter to permit insertion of distal shaft end 54 through the vascular system and into ventricle 14 (FIG. 1). Manifold 30 preferably has a length of about 0.2 inches.

A proximal portion of shaft 32 can be augmented with additional design features well known to those skilled in the art to provide adequate steerability, size, pushability, tracking, and biocompatibility. In addition, the catheter polymer material forming shaft 32 can include a radiopaque filler material well known in the art (e.g., bismuth subcarbonate or barium sulfate) to facilitate visualization of catheter shaft 32 under fluoroscopy.

As shown in FIG. 2, shaft 32 also includes temperature sensing lumen 56, and microwave antenna lumen 58. Lumens 56 and 58 generally extend from proximal shaft end 50 to distal shaft end 54.

Temperature sensing lumen 56 is positioned near first side 60 of shaft 32. Temperature sensing lumen 56 permits insertion of thermometry sensor 37 within shaft 32 to monitor the temperature of adjacent tissue when shaft 32 is inserted within ventricle 14. Sensor 37 exits through manifold 30 and is connected to thermometry unit 42. In a preferred embodiment, thermometry sensor 37 is a fiber optic luminescence type temperature sensor sold by Luxtron Corporation.

Microwave antenna lumen 58 is aligned centrally relative to the longitudinal axis of shaft 32 along a majority of the length of shaft 32, antenna lumen 58 being equidistant between first side 60 of shaft 32 and second side 62 of shaft 32. However, at the distal-most end of shaft 32, adjacent cooling balloon 36, antenna lumen 58 effectively becomes oriented nearer first side 60 than second side 62 due to the presence of cooling balloon 36. At its proximal end, antenna lumen 58 communicates with manifold 30.

Antenna lumen 58 is adapted for receiving microwave antenna 34 to be permanently positioned within antenna lumen 58 near cooling balloon 36 so that antenna 34 will be generally situated adjacent damaged tissue 20 of ventricle wall 16 when shaft 32 is properly positioned within heart 10. Antenna 34 can be bonded within antenna lumen 58 by an adhesive bond and is carried at the distal-most end of coaxial cable 41. The proximal-most end of coaxial cable 41 is connected to microwave generating source 40. Microwave generating source 40 produces high frequency microwaves, preferably at about 915 MHz. When antenna 34 is energized by microwave generating source 40, antenna 34 emits electromagnetic energy which causes heating of tissue within ventricle wall 16 at target location 20 (FIG. 1).

Cooling balloon 36 cooperates with multi-lumen shaft and is secured about distal end 54 of catheter shaft 32. Cooling balloon 36 is provided so that when filled with a cooling fluid, cooling balloon 36 absorbs microwave energy emitted by antenna 34 to prevent unwanted heating of blood on second side 62 of catheter 28 within a cardiac chamber of the heart while microwave energy radiating from a first side of catheter 28 heats damaged tissue 20. Cooling balloon 36 cools blood immediately surrounding and passing by the cooling balloon 36.

Cooling balloon 36 includes distal tip end 70, expandable wall portion 72, connection portion 73 and proximal waist end 74. Balloon 36 is secured over shaft 32 by slip-fitting balloon 36 over the distal end 54 of the catheter shaft 32. Distal tip end 70 of balloon 36 is then adhesively bonded to exterior surface 52 of shaft 32 at distal shaft end 54. Connection portion 73 of cooling balloon 36 is adhesively bonded to outer surface 52 on shaft first side 60 while proximal waist 74 of cooling balloon 36 is adhesive bonded to outer surface 52 on both shaft sides 60 and 62.

This arrangement creates a sealed connection at distal end 70, proximal end 74, and along connection portion 73 to secure cooling balloon 36 on catheter shaft 32. An inner surface of expandable portion 72 is spaced from and is not secured to shaft outer surface 52 so that expandable portion 72 remains free to expand relative to catheter outer surface 52 upon introduction and passage of an inflation cooling fluid through an interior of cooling balloon 36. With cooling balloon 36 secured in this manner, outer surface 52 of catheter second side 62 and expandable portion 72 effectively define a cooling chamber which can be inflated (as seen in FIG. 2) and deflated (shown in phantom in FIG. 2) by the selective introduction and removal of an inflation fluid within an interior of expandable wall portion 72. Expandable portion 72 of cooling balloon 36 is positioned adjacent to microwave antenna 34 so that in use, cooling fluid within cooling balloon 36 will cool blood surrounding catheter second side 62 and absorb microwave energy radiating towards second side 62 when antenna 35 is energized.

Cooling balloon 36 extends for a length adjacent distal shaft end 54 that is substantially less than the length of catheter shaft 32, yet equal to or greater than a length of microwave antenna 34. Moreover, cooling balloon 36 has a length less than an entire length of the ventricle wall (shown in FIG. 1). For example, cooling balloon 36 preferably has a length of about 1 to 2.5 centimeters with expandable wall portion 72 preferably having a length of about 0.5 to 2 centimeters. Balloon 36 is a flexible tubular member formed of PET, cross-linked polyethylene or some other thermoplastic material that acts as a low-compliance balloon material.

Figure 3:
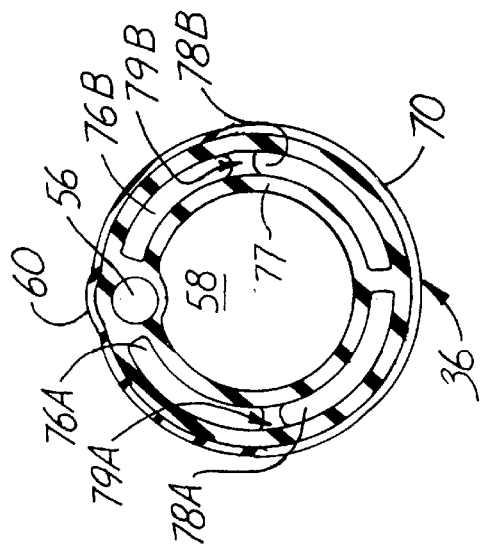
FIG. 3 is a sectional view of a shaft of the catheter of FIG. 2 taken along lines 3—3.

Cooling balloon 36 cooperates with multi-lumen shaft 32. As shown in FIG. 3, shaft 32 further includes cooling lumens 76A, 76B and cooling lumens 78A, 78B in addition to temperature sensing lumen 56 and antenna lumen 58. Temperature sensing lumen 56 preferably has a generally circular shaped transverse cross-section with a diameter of about 0.02 inches and an outer surface radius (defined by outer surface 52) of about 0.013 inches. Microwave antenna lumen 58 preferably has a generally circular shaped transverse cross-sectional area which is substantially larger than a transverse cross-sectional area of any other respective lumen of catheter shaft 32. Antenna lumen 58 preferably has a diameter of about 0.060 inches.

Cooling fluid intake lumens 76A, 76B are positioned adjacent shaft first side 60 between first side 60 and antenna lumen 58 while cooling fluid exhaust lumens 78A, 78B are positioned adjacent shaft second side 62 between second side 62 and antenna lumen 58. Cooling fluid intake lumens 76A, 76B and exhaust lumens 78A, 78B extend from proximal shaft end 50 to distal shaft end 54 where lumens 76A, 76B and 78A, 78B terminate. Cooling fluid intake lumens 76A, 76B and exhaust lumens 78A, 78B are defined by single wall 77 having a uniform thickness and preferably have a generally arc shaped transverse cross-section configured to surround antenna lumen 58. Cooling lumens 76A, 76B and 78A, 78B preferably have a uniform radial thickness of about 0.010 inches defined by an inner radius of about 0.035 inches and an outer radius of about 0.045 inches. In combination, cooling lumens 76A, 76B and cooling lumens 78A, 78B substantially surround antenna lumen 58 about a substantial majority (about 75%) of a circumference of antenna lumen 58. Cooling lumens 76A, 76B and 78A, 78B surround antenna lumen 58, so that when filled with a cooling fluid, cooling exhaust lumens 78A and 78B absorb microwave energy emitted by antenna 34 (within antenna lumen 58) to protect blood immediately surrounding catheter shaft second side 62 and cooling intake lumens 76A, 76B cool tissues immediately adjacent catheter shaft first side 60.

Figure 4:
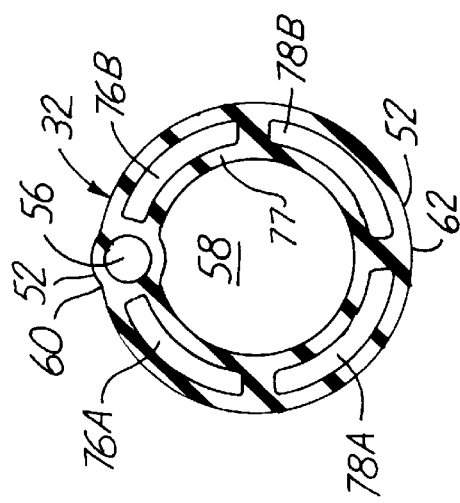
FIG. 4 is a sectional view of the catheter shaft of FIG. 2 taken along lines 4—4.

Cooling fluid intake lumens 76A and 76B communicate with cooling exhaust lumens 78A and 78B, respectively, near distal shaft end 54 of catheter shaft 32 distal to expandable portion 72 of cooling balloon 36 (FIG. 2). As shown in FIG. 4, catheter wall 77 includes holes 79A and 79B and distal portion 70 of cooling balloon 36 is secured to catheter shaft outer surface 52. Hole 79A in catheter wall 77 permits communication between cooling intake lumen 76A and cooling exhaust lumen 78A while hole 79B in catheter wall 77 permits communication between cooling intake lumen 76B and cooling exhaust lumen 78B. Cooling intakes lumens 76A and 76B and cooling exhaust lumens 78A and 78B cooperate with cooling system 38 (via manifold 30) to provide a selectively controlled flow of fluid through cooling lumens 76A, 76B, 78A, and 78B during a treatment session. For example, in one embodiment, intake lumens 76A, 76B and exhaust lumens 78A, 78B are supplied with deionized water from cooling system 38. Water from cooling system 38 is chilled to between about 12°–15° C. and pumped through cooling fluid intake lumens 76A, 76B toward distal shaft end 54. Under fluid pressure, water enters cooling fluid exhaust lumens 78A, 78B through holes 79A, 79B and returns to cooling system 38 through exhaust lumens 78A, 78B for re-chilling and re-circulation.

Figure 5A:
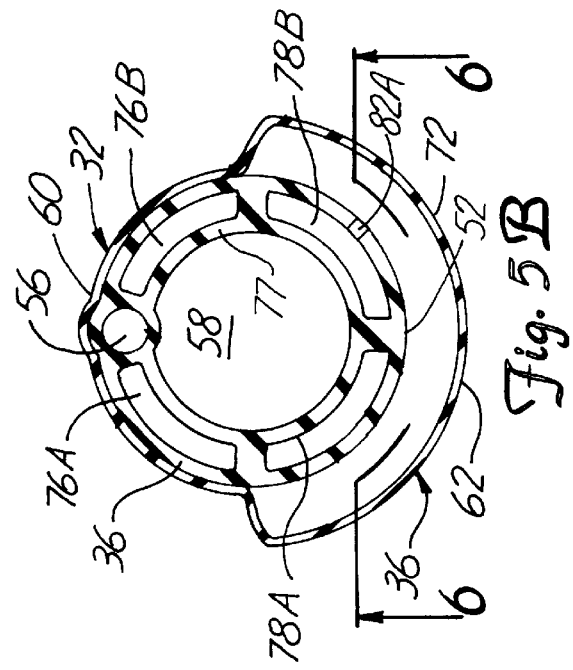
FIG. 5A is a sectional view of the catheter shaft of FIG. 2 taken along lines 5A—5A.
Figure 5B:
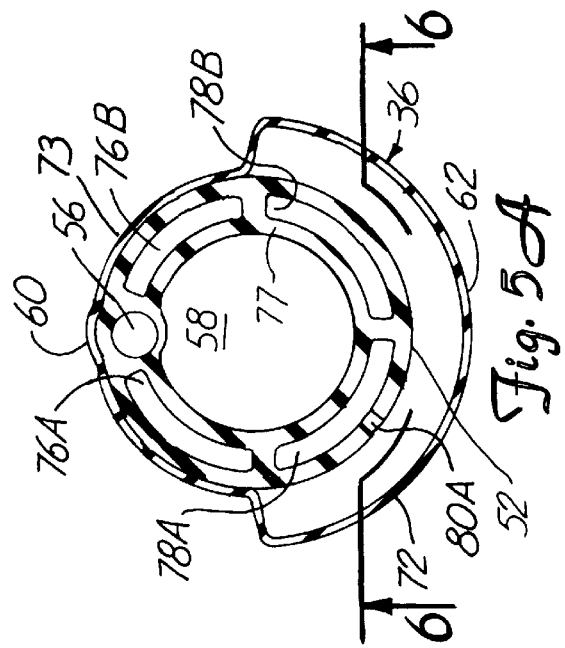
FIG. 5B is a sectional view of the catheter shaft of FIG. 2 taken along lines 5B—5B.

FIGS. 5A and 5B illustrate communication between cooling balloon 36 and cooling exhaust lumens 78A, 78B. FIGS. 5A and 5B are cross-sectional views of shaft 32 taken along lines 5A—5A and 5B—5B in FIG. 2. As seen in FIG. 5A, cooling balloon 36 surrounds shaft outer surface 52 on shaft second side 62 with expandable portion 72 preferably having a generally arc shaped transverse cross-section (when inflated). Connection portion 73 of cooling balloon 36 is secured to shaft first side 60 while expandable portion 72 is spaced from and substantially surrounds entire second side 62 including cooling fluid exhaust lumens 78A, 78B. Cooling balloon 36 has a wall thickness of about 0.0005 to 0.005 inches, which is generally less than a wall thickness of wall 77 (e.g., 0.005 inches) defining cooling lumens 76A–78B. The cooling chamber defined between catheter outer surface 52 and expandable portion 72 of cooling balloon 36 has a radial thickness of about 0.5 to 5.0 millimeters, which is substantially greater than a radial thickness of cooling exhaust lumens 78A, 78B (e.g., 0.25 millimeters). Accordingly, expandable portion 72 of cooling balloon 36 (when inflated) defines a cooling chamber that has a transverse cross-sectional area substantially greater than the transverse cross-sectional area of cooling exhaust lumens 78A, 78B.

As further shown in FIG. 5A, an outer wall of cooling exhaust lumen 78A includes hole 80A and as shown in FIG. 5B, an outer wall of cooling exhaust lumen 78B includes hole 82A. Hole 80A permits communication between exhaust lumen 78A and an interior of cooling balloon 36 while hole 82A permits communication between an interior of cooling balloon 36 and exhaust lumen 78B. Since fluid is flowing under pressure into cooling lumens 78A and 78B, fluid within lumen 78A enters inflatable cooling balloon 36 via hole 80A, passes through cooling balloon 36 and exits into exhaust lumen 78B via hole 82A to recirculate through cooling system 38 via manifold 30. As shown in FIG. 6, holes 80A and 80B are both axially and laterally spaced apart. This arrangement creates a pressure differential between the respective holes 80A and 80B causing a passive inflation of the cooling balloon 36 and insuring that adequate fluid circulation will occur through cooling balloon 36 as cooling fluid moves through cooling lumens 76A, 76B and 78A, 78B.

In addition, the rate of cooling fluid intake into lumens 76A, 76B and the rate of cooling fluid exhaust out of lumens 78A, 78B can be manipulated by cooling system 38 via manifold 30 to selectively modify the fluid pressure gradient between hole 80A and hole 80B to maintain cooling balloon 36 in an inflated state and to ensure a constant circulation of cooling fluid therethrough. The relative sizing of holes 80A and 80B, respectively, also can be modified to control the flow of cooling fluid in and out of the cooling balloon 36. For example, hole 80A can be made larger than hole 80B to accentuate filling of cooling balloon 36.

The microwave radiation used to ablate target tissue 20 (FIG. 1) is emitted by microwave antenna 34. FIG. 7 illustrates microwave antenna 34 in detail. Microwave antenna 34 is adapted for employment in cardiovascular applications and therefore is designed to have a low profile (minimal outer diameter) while still providing efficient powerful emission of microwave energy to selectively ablate targeted cardiac tissue 20. In particular, antenna 34 is designed so that an outer diameter of antenna 34 is no greater than an outer diameter of coaxial cable 41, and so that antenna 34 is relatively short, e.g., about 2–3 centimeters. As previously described, microwave antenna 34 is positioned within microwave antenna lumen 58 and is surrounded by cooling lumens 76A, 76B, 78A, 78B and cooling balloon 36.

FIG. 7 illustrates a sectional view of microwave antenna 34. Antenna 34 is positioned at the distal most end of shielded coaxial cable 41. Cable 41 is a standard miniature 30 AWG or 32 AWG coaxial cable and can be obtained from CoonerWire of Chatsworth, Calif. Coaxial cable 41 includes inner conductor 100, inner insulator 102, outer conductor 104, and outer insulator 106. Antenna 34 further includes transition portion 108, reduced diameter portion 110 of inner insulator 102, first tubular extension 112, second tubular extension 114, and annular collar 116. Antenna 34 also includes a flat wire coil 118, capacitor 120, solder 122, and end cap 124.

First tubular extension 112 encompasses outer conductor 104 and reduced diameter portion 110 of inner insulator 102. A proximal end of tubular extension 112 is positioned adjacent transition portion 108 of cable 41. Annular collar 116 also encompasses outer conductor 104 and reduced diameter portion 110 of inner insulator 102 and abuts a distal end of tubular extension 112. Annular collar 116 is a conductive material that is in electrical contact with outer conductor 104. Second tubular extension 114 also encompasses outer conductor 104 and reduced diameter portion 110 of inner insulator 102 with a proximal end of second tubular extension 114 abutting annular collar 116. A distal end of second tubular extension 114 has end cap 124 disposed therein.

Flat wire 118 forms a coil about tubular extensions 112 and 114. Capacitor 120 is secured about a distal end of inner conductor 100 and is further electrically connected to flat wire coil 118 by solder 122 extending through hole 126.

Reduced diameter portion 110 preferably has a length of about 2 inches and an outer diameter of about 0.05 inches. Tubular extensions 112 and 114 have lengths of 1 inches and 0.8 inches, respectively, and can have a thickness of about 0.010 inches. Reduced diameter portion 110 and tubular extensions 112 and 114 have outer diameters (or thicknesses) of a size so that when antenna 34 is fully constructed, antenna 34 has an outer diameter of about 0.060 inches or less.

Antenna 34 includes a first coil section 140 and a second coil section 142, both of which are of equal length. These two sections are created by the electrical connection of annular collar 116 with flat wire coil 118 at a midsection of flat wire coil 118. In one embodiment, first and second coil sections 140 and 142 are each comprised of five equally-spaced windings of flat wire coil 118 about tubular extensions 112 and 114, respectively. The combined length of first and second coil sections 140 and 142 provide an overall length of antenna 34 of about 2 centimeters. However, this overall length and the number of windings of the coil can be varied as needed to provide the desired length of antenna coil 118.

In one embodiment of the present invention, flat wire 118 is made of a flat ribbon of copper or silver and can be plated with a highly conductive material. The ribbon can be 0.02 inches wide and 0.006 inches thick. Flat wire 118 has a physical length of 4.5 inches, which when coiled provides a total length for first coil wire section 140 and second coil wire section 142 of 2 centimeters.

The location along coil 118 of an electrical connection between first coil section 140 and capacitor 120 corresponds to a tap point used for impedance matching. Specifically, a tap point is selected along coil 118 so that an impedance presented between the tap point and annular collar 116 (corresponding to the point of electrical connection between coil 118 and inner conductor 100) matches the characteristic impedance of coaxial cable 41. As shown in FIG. 7, in this embodiment, the tap point is located adjacent the end of first coil section 140 of coil 118. However, the tap point can be located nearer to annular collar 116 as necessary to obtain the required impedance match.

The impedance of either first coil section 140 or second coil section 142 also includes an inductive component which is eliminated by providing a series capacitance such as capacitor 120. Accordingly, tubular capacitor 120 serves to counteract a reactive component of antenna 34, thereby providing a fifty (50) Ohm resistive impedance match between coaxial cable 41, microwave generating source 40, and antenna 34.

Tubular capacitor 120 preferably has a value of about 2.7 pF and can be obtained from Coors Ceramics Co. of Golden, Colo. Capacitor 120 and preferably is sized to fit over an inner conductor 100 having an inner diameter of about 0.089 to 0.012 inches has a length of 0.125 inches, an outer diameter of about 0.045 inches, and an inner diameter of about 0.025 inches. Tubular capacitor 120 is substantially similar in design to a tubular capacitor described and shown in Rudie et al. U.S. Pat. No. 5,370,677, which is hereby incorporated by reference, and is mounted and connected to the inner conductor 100 and flat wire antenna coil 118 in a manner substantially similar to that described in Rudie et al. U.S. Pat. No. 5,370,677.

While the preferred dimensions for reduced diameter portion 110 have been identified above, the relatively smaller radial dimensions of reduced diameter portion 110 of inner insulator 102 could result in a characteristic impedance different than 50 Ohms. The characteristic impedance (Zo) can be calculated with the following equation:

$$Z_o = \frac{138}{\sqrt{\epsilon_r}} \log_{10}\left(\frac{D}{d}\right)$$

where $\epsilon_r$ is the relative dielectric constant of the inner insulator 102, D is the inner diameter of outer conductor 104, and d is the outer diameter of inner conductor 100. Accordingly, a characteristic impedance of 50 Ohms can be maintained with a reduced diameter portion 110 by adjusting the ratio of D/d (e.g., reducing d), by selecting an appropriate relative dielectric constant ($\epsilon_r$), or by adjusting both the ratio D/d and the relative dielectric constant ($\epsilon_r$). Alternatively, any resulting impedance mismatch resulting from the altered diameter of reduced diameter portion 110 of inner insulator 102 can be remedied by selecting an appropriate tap point location and a corresponding capacitor value for capacitor 120.

Finally, antenna 34 can include platinum or gold bands located adjacent either or both ends of the flat wire antenna coil 118 to facilitate positioning of antenna 34 and catheter 28 within the cardiovascular system since the gold bands will substantially improve visualization of antenna 34 under fluoroscopy.

Antenna 34 generally has a helical dipole construction similar to the helical dipole construction of a microwave antenna described and shown in Rudie et al., U.S. Pat. Nos. 5,300,099 and 5,370,677, which are hereby incorporated by reference. Accordingly, the helical dipole construction of antenna 34 of the present invention has an effective electrical length generally equal to one-half of the wave length of the radiation emitted in the surrounding medium, e.g., the catheter shaft and surrounding tissue. Because of the helical dipole construction of antenna 34, in accordance with Rudie U.S. Pat. Nos. 5,300,099 and 5,370,677, antenna 34 can have different physical lengths yet have the same effective electrical length to produce a consistent and predictable pattern of radiation.

However, microwave antenna 34 of the present invention has its own unique advantages. Foremost, in order to minimize the profile of the cardiovascular catheter 28 and antenna 34 located therein, the antenna 34 and coaxial cable 41 are configured and arranged so that the antenna 34 has an outer diameter that is no greater than an outer diameter of the coaxial cable 41. This arrangement is achieved through a combination of features. First, inner insulator 102 is modified adjacent a distal end of coaxial cable 41 into a reduced diameter portion 110 along the length of the antenna 34, and outer insulator 106 of coaxial cable 41 is replaced with outer insulating tube sections 112 and 114. Second, flat wire coil 118 is located distally beyond the end of outer insulator 106 of coaxial cable 41 so that no portion of coil 118 extends about outer insulator 106 of coaxial cable 41.

However, with this arrangement, the point of electrical connection between inner conductor 104 and coil 118 can no longer be placed on the outer insulator 106 (as in the Rudie et al. patents) but instead needs to be located distally beyond a distal end of outer insulator 106. Accordingly, annular collar 116 is positioned to serve as the point of electrical connection between inner conductor 100 and coil 118 with outer insulator tube sections 112 and 114 being positioned on opposite sides of annular collar 116.

In combination, these modifications to the antenna disclosed in Rudie et al. U.S. Pat. Nos. 5,300,099 and 5,370,677 produce a microwave antenna 34 of the present invention that has substantially the same operating characteristics of the antenna disclosed in the Rudie et al. patents yet has an outer diameter no greater than an outer diameter of coaxial cable 41 to provide a low profile for cardiovascular and arterial applications. The antenna 34 also has a physical length which has been minimized to improve the maneuverability of the catheter 28.

Figure 8:
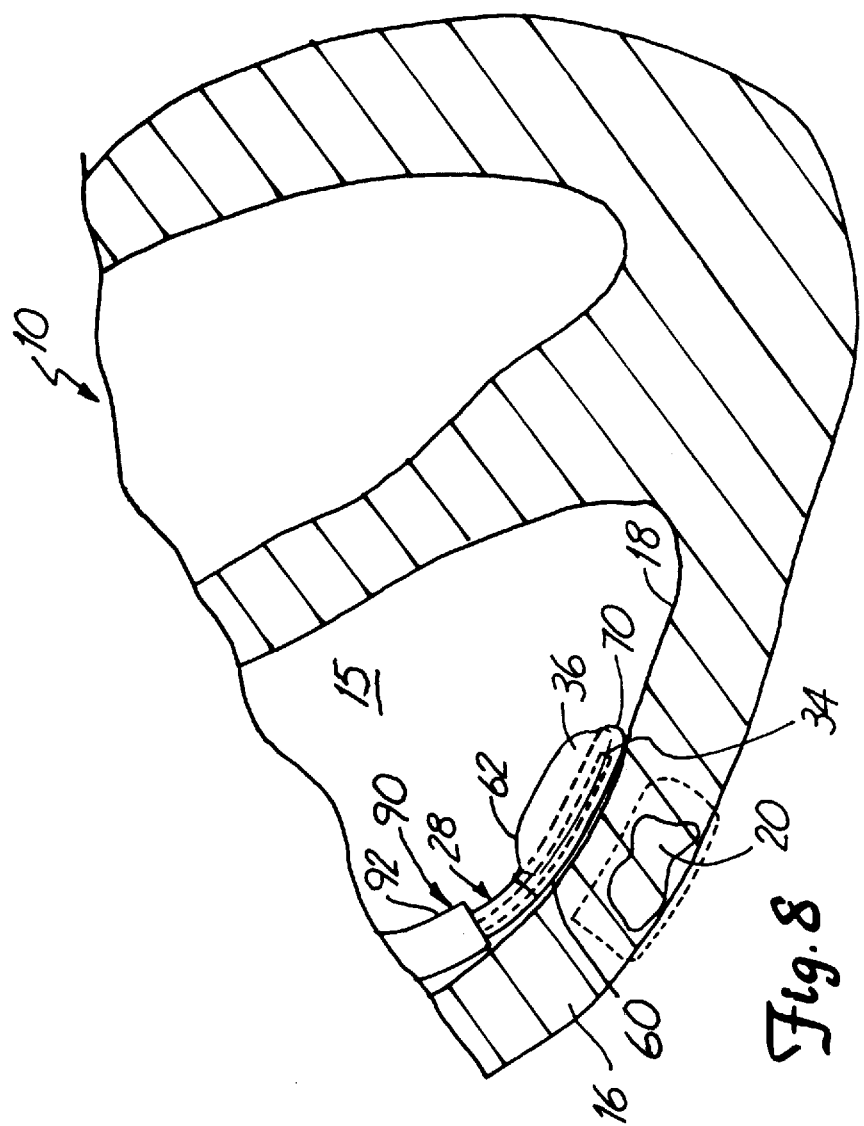
FIG. 8 is a partial sectional view of a catheter of the present invention as disposed within a ventricle of a heart for applying microwave thermal ablation therapy to the ventricle wall.

FIG. 8 shows an enlarged view of the ventricle 14 of FIG. 1 with catheter 28 properly positioned within ventricle 14. In use, catheter 28 is maneuvered into ventricle 14 through guide catheter 90. Guide catheter 90 has a design suitable for passage through a vascular system, so that a distal end 92 of guide catheter 90 can rest supportedly adjacent ventricle wall 16 to stably support catheter 28 adjacent wall 16.

Catheter 28 is inserted into guide catheter 90 from outside the body at a remote location (e.g., femoral artery) in a manner well known in the art. Catheter 28 is advanced through guide catheter 90 with cooling balloon 36 in its deflated state (shown in phantom in FIG. 2), which provides catheter 28 with a low profile to facilitate insertion and advancement of catheter 28 through guide catheter 90. Catheter shaft 28 is advanced through guide catheter 90 until distal end 54 is positioned within ventricle 14 as shown in FIG. 8. In this position, first side 60 of shaft 32 and cooling fluid intake lumens 76A, 76B are oriented toward ventricle wall 16 while second side 62 of shaft 32 with cooling fluid exhaust lumens 78A, 78B and cooling balloon 36 are oriented toward blood 15.

Next, cooling system 38 is operated to provide a continuous flow of cooling fluid through cooling fluid intake lumens 76A, 76B, cooling fluid exhaust lumens 78A, 78B, and cooling balloon 36. Cooling balloon 36 is inflated by the fluid through holes 80A and 82A from cooling exhaust lumens 78A and 78B.

At this point, microwave energy is selectively directed into target tissue 20 by energizing microwave antenna 34 with microwave generating source 40. Since cooling fluid exhaust lumens 78A, 78B and cooling balloon 36 absorb significant amounts of microwave energy while cooling fluid intake lumens 76A, 76B, absorb very little radiation, the radiation pattern applied to the surrounding tissues becomes asymmetrical with large amounts of microwave energy acting on target tissue 20 and almost no microwave energy acting on blood 15. As a result, a relatively large volume of tissue enveloping the damaged target tissue 20, adjacent catheter first side 60, is heated according to a time and temperature relationship that effectively necroses the damaged tissue 20 of ventricle wall 16 (which causes cardiac arrhythmias). In comparison, blood adjacent second side 62 remains below a necrosing time and temperature exposure, thereby eliminating the harmful effects of the heat (generated by microwave energy) to blood 15 and the remaining healthy structures of ventricle 14. For a complete discussion on the time and temperature relationship for causing necrosis of tissues, see Dickson et. al., Thermosensitivity of Neoplastic Tissues In Vivo, HYPERTHERMIA IN CANCER THERAPY, Chapter 5 (1983).

This preferential heating pattern created by catheter 28 allows microwave energy to be concentrated only at selective locations deep within the ventricle wall 16 (e.g., up to 2 cm) at damaged tissue 20 while protecting healthy tissues (e.g., blood 15) from necrosing temperatures (e.g., above 45° C.). After a desired amount of microwave energy has been applied to the damaged tissue 20 and the surrounding tissues have been allowed to return to normal body temperature, cooling system 38 can be turned off thereby permitting deflation of the cooling balloon 36. Once the cooling balloon 36 is deflated, the catheter 28 can be removed from ventricle 14 proximally through the guide catheter 90.

Intravascular catheter 28 of the present invention can be used as part of an intravascular microwave thermal therapy system substantially similar to the transurethral microwave thermal therapy system described and shown in Rudie et al. U.S. Pat. No. 5,413,588 and hereby incorporated by reference.

The catheter of the present invention permits the application of microwave energy in a cardiovascular environment to ablate tissue lesions located deep (e.g., 2 cm) below a surface of the tissue without causing necrosis of surrounding healthy tissues. This capability is achieved by a combination of features including, amongst others, an efficient dipole helical antenna design and a microwave energy absorbing system. The antenna of the present invention minimizes reflective losses, provides good current carrying capability, and has an effective electrical length that can remain consistent despite different physical lengths of the antenna. The microwave energy absorbing system includes a pair of cooling fluid intake lumens, a pair of exhaust lumens and a cooling balloon, which complements the cooling exhaust lumens.

Performing a thermal therapy treatment on a cardiac wall with catheter 28 of the present invention has considerable advantages. Cooling balloon 36 in combination with cooling exhaust lumens 78A, 78B enables cooling fluid within catheter 28 to cool blood immediately adjacent catheter second side 62 via thermal conduction. At the same time, the cooling fluid within cooling balloon 36 and within cooling exhaust lumens 78A, 78B, absorbs a substantial amount of microwave energy (when microwave antenna 34 within antenna lumen 58 is energized) so that the temperature of blood adjacent second side 62 of shaft 32 will remain below a necrosing temperature as desired (e.g., below 45° C.). In combination, the relatively large radial dimensions of the cooling balloon 36, and its relative position adjacent a microwave antenna on second side 62 of catheter 28 provides a cooling chamber that protects blood when a microwave antenna within lumen 58 is energized. Conversely, high levels of microwave energy are directed beyond the ventricle wall surface 18 into the ventricle wall 16 as cooling intake lumens 76A, 76B protect wall surface 18 from thermal damage without substantially absorbing microwave radiation directed toward target tissues. This enables tissue in target region 20 (FIG. 8) deep below the ventricle wall surface to be adequately necrosed while at the same time preserving blood passing by a side of the catheter opposite the target location.

In addition, cooling balloon 36 accentuates thermal conduction between cooling fluid within cooling balloon 36 and blood flowing through the ventricle since cooling balloon 36 has a wall thickness less than the cooling exhaust lumens 78A, 78B. This feature places cooling fluid into closer contact with blood within the ventricle thereby improving heat transfer away from blood within the ventricle.

The presence of cooling balloon 36 also effectively makes antenna lumen 58 nearer to shaft first side 60 than shaft second side 62 (adjacent distal shaft end 54), so that antenna lumen 58 becomes eccentric to a longitudinal axis of catheter 28 adjacent distal shaft end 54. This orientation effectively moves antenna 34 further away from blood adjacent shaft second side 62 to further reduce unwanted heating of blood 15.

The cooling balloon is capable of being deflated as well as inflated. When deflated, the cooling balloon gives the catheter an overall low profile which facilitates insertion and advancement of the catheter through the cardiovascular system for deployment in distally remote locations, e.g., arteries and chambers of the heart. Moreover, cooling balloon 36 surrounds catheter shaft 32 with expandable portion 82 being the only portion of cooling balloon 36 spaced from catheter outer surface 53. This arrangement permits deflated cooling balloon 36 to have a low profile making cooling balloon 36 highly resistant to separation from the catheter shaft 32 and facilitating rotation of catheter 28 within urethra 10. This arrangement also simplifies the need for an elaborate system to wrap balloon 36 in deflated state. Finally, the cooling balloon conveniently slip fits over the distal tip of the catheter shaft thereby permitting easy manufacture of the catheter and ensuring that the balloon is properly sealed against the catheter shaft to allow proper inflation and deflation.

In an alternate embodiment, interior surface of cooling balloon 36 can include a coating capable of reflecting microwave energy from antenna 34, which these can further reduce the amount of microwave energy directed outwardly on the catheter second side 62. Such coating materials can also be incorporated into shaft 32 as necessary to further prevent the emission of microwave energy in undesired locations. For example, the coating material could be incorporated into the distal tip end of shaft 32 or along the shaft 32 proximal of antenna 34 to minimize unwanted emission of microwave energy in those areas.

Alternative embodiments of a catheter of the present invention are illustrated in FIGS. 9–14. Catheter 160 shown in FIG. 9 has all the attributes and features of catheter 28 shown in FIGS. 2–8 except that catheter 160 includes a modified structure for communication between cooling exhaust lumens and a cooling balloon. Specifically, instead of the structure shown in FIG. 6, catheter 160 shown in FIG. 9 includes catheter shaft 161 having cooling exhaust lumens 166A and 166B, cooling balloon 168, and a first pair of holes 170A, 170B and a second pair of holes 172A, 172B. An outer wall of cooling exhaust lumen 166A includes holes 170A and 170B, which permit communication between cooling exhaust lumen 166A and an interior of cooling balloon 168. An outer wall of cooling exhaust lumen 166B includes holes 172A and 172B which permit communication between an interior of cooling balloon 168 and cooling exhaust lumen 166B. Cooling fluid enters cooling balloon 168 through holes 170A, 172A and exits cooling balloon 168 through holes 170B, 172B.

Catheter 160 further includes restrictor 176A located between holes 170A and 170B and restrictor 176B between holes 172A and 172B, as shown in FIG. 10. For illustration purposes, only restrictor 176A located between holes 170A and 170B is shown. Restrictor 176A is positioned on an outer wall of cooling exhaust lumen 166A at a location selected to create a pressure differential between holes 170A, 170B thereby causing passive inflation and active circulation of fluid through cooling balloon 168. Restrictor 176A as shown in FIG. 10, is preferably located immediately adjacent hole 170A and proximal to antenna 178 so that the restrictor 176B does not affect a near field radiation emitted by the antenna 178. However, the restrictor 176A can be located at a more distal location adjacent the antenna 178 if desired. Restrictor 176A is formed and added to cooling exhaust lumen 166A by depositing adhesive on an inner surface of an outer wall of cooling exhaust lumen 166A at a desired location. Restrictor 176B is situated similar to restrictor 176A except being located between holes 172A and 172B in cooling exhaust lumen 166B.

In use, cooling fluid passing through cooling exhaust lumens 166A, 166B enters cooling balloon 168 through holes 170A and 172A thereby permitting passive inflation of cooling balloon 168. Restrictors 176A and 176B accentuate passive inflation of cooling balloon 168 and circulation of fluid therethrough by creating a pressure differential between holes 170A and 170B and between holes 172A and 172B. Holes 170B and 172B permit fluid to exit cooling balloon 168 into cooling exhaust lumens 166A and 166B for recirculation through a cooling system of catheter 160 (not shown).

FIG. 11 shows another modified catheter 180 of the present invention. Catheter 180 has all the attributes and features of catheter 28 shown in FIGS. 2–8 except that catheter 180 also includes a modified structure for communication between cooling exhaust lumens and cooling balloon 184. Specifically, instead of the structure shown in FIG. 6, catheter 180 includes catheter shaft 181 having cooling exhaust lumens 182A and 182B, cooling balloon 184, and a first slot 186 and a second slot 188. Slot 186 is an elongate hole formed in the side wall of catheter shaft defining exhaust lumen 182A while slot 186 is an elongate hole formed in the side wall of catheter shaft defining exhaust lumen 182B. Slot 186 permits unrestricted communication between cooling exhaust lumen 182A and an interior of cooling balloon 184 while slot 188 permits unrestricted communication between cooling exhaust lumen 182B and an interior of cooling balloon 184. This unrestricted communication facilitates relatively turbulent flow of cooling fluid within cooling balloon 184 thereby assuring active circulation of cooling fluid through the cooling balloon 184. Cooling balloon 184 is passively inflated and maintained in that state by controlling the rate of fluid flow into the cooling intake lumens (not shown) and the rate of fluid flow out of the cooling exhaust lumens 182A and 182B.

Figure 13:
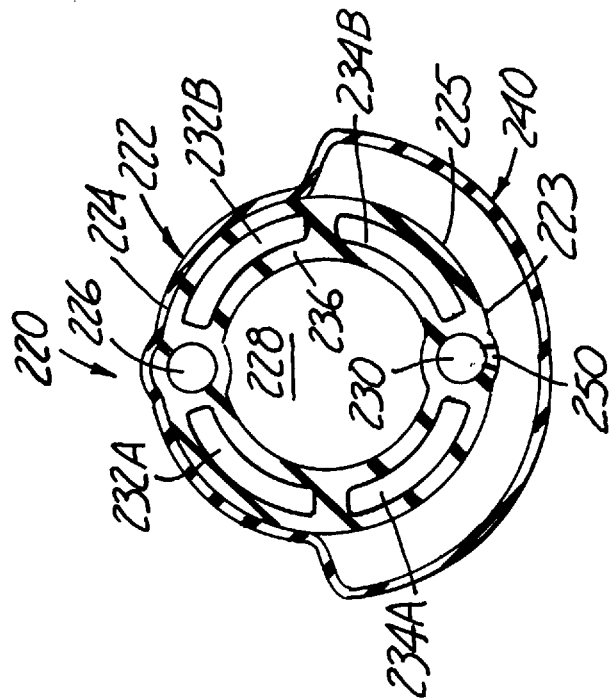
FIG. 13 is a sectional view of a shaft of an alternate embodiment of the catheter, similar to the view shown in FIG. 5A.
Figure 12:
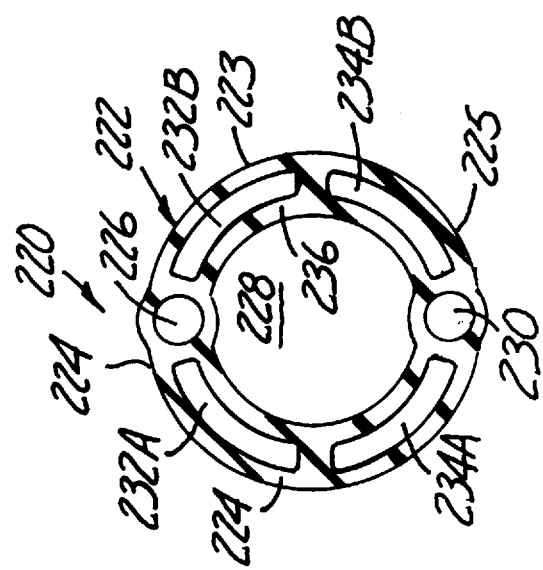
FIG. 12 is a sectional view of a shaft of an alternate embodiment of the catheter, similar to the view shown in FIG. 3.

Another embodiment of the present invention is shown in FIGS. 12–13. Catheter 220 is similar to catheter 29 of the present invention (shown in FIGS. 2–8) and has all the attributes and features of catheter 28 except that catheter 220 includes a fluid lumen for inflating a cooling balloon that is independent of cooling exhaust lumens of the catheter. As shown in FIG. 12, catheter 220 generally includes multi-lumen shaft 222 having outer surface 223 with first side 224 and second side 225. Shaft 222 also has a distal end and a proximal end similar to those shown for catheter 28 in FIG. 2. Distal end of shaft 222 is connected to a manifold for communication and operation with a complete thermal therapy system as previously described for catheter 28.

As shown in FIG. 12, multi-lumen shaft 222 includes temperature sensing lumen 226, microwave antenna lumen 228, cooling balloon inflation lumen 230, cooling fluid intake lumens 232A and 232B, and cooling exhaust lumens 234A and 234B. Lumens 226–234B are similar to the corresponding temperature sensing lumen 56, microwave antenna 58, cooling lumens 64A, 64B previously described for catheter 28 in association with FIG. 3. However, unlike catheter 28, catheter 220 further includes a cooling balloon inflation lumen 230 and includes cooling exhaust lumens 234A, 234B which have slightly different dimensions than cooling exhaust lumens 78A, 78B of catheter 28 (FIG. 3).

Cooling balloon inflation lumen 230 is positioned between cooling exhaust lumens 234A and 234B adjacent second side 225 on an opposite side of antenna lumen 228 from temperature sensing lumen 226. Cooling balloon inflation lumen 230 preferably has a generally circular cross-sectional shape with a diameter of about 0.040 inches. Cooling balloon inflation lumen 230 communicates with an inflation port in a manifold to permit inflation and deflation of cooling balloon 250.

Cooling fluid intake lumens 232A, 232B are positioned adjacent shaft first side 224 and have all the attributes and features of cooling intake lumens 64A, 64B (FIG. 3). Cooling fluid exhaust lumens 234A, 234B are positioned adjacent shaft second side 225 and have all the attributes and features of cooling exhaust lumens 66A, 66B except having a smaller arc to accommodate cooling inflation lumens 230 positioned between lumens 234A and 234B. In addition, cooling exhaust lumens 234A, 234B lack holes in their outer walls similar to holes 80A and 80B in cooling lumens 66A, 66B. (FIG. 6).

Cooling fluid intake lumens 232A and 232B communicate with cooling exhaust lumens 234A and 234B, respectively, near a proximal end of catheter shaft 232. Cooling intake lumens 232A and 232B and cooling exhaust lumens 234A and 234B cooperate with a cooling system via manifold to provide a selectively controlled flow of fluid from cooling intake lumens 232A, 232B into cooling exhaust lumens 234A, and 234B during a treatment session. Fluid contained within exhaust lumens 234A and 234B selectively absorbs a portion of microwave energy emitted by a microwave antenna within antenna lumen 228 and cools tissue surrounding shaft second side 225 to aid in controlling the temperature of tissue adjacent catheter shaft second side 225 below necrosing levels (e.g., below 45° C.).

As further shown in FIG. 13, cooling balloon 240 surrounds shaft outer surface 223 on shaft second side 225. Cooling balloon 240 has all the attributes and features of cooling balloon 36 of catheter 28 (as previously described in association with FIGS. 2–8). As shown in FIG. 13, an outer wall of cooling balloon inflation lumen 230 includes hole 250. Hole 250 permits communication between cooling balloon inflation lumen 230 and an interior of cooling balloon 240 (shown inflated in FIG. 13). Accordingly, cooling balloon 240 is filled and inflated by the introduction of cooling fluid from cooling balloon inflation lumen 230 through hole 250.

Cooling inflation lumen 230 is independent of cooling exhaust lumens 234A, 234B enabling cooling balloon 240 to be inflated and deflated independently of fluid flow within cooling exhaust lumens 234A, 234B. This relationship provides an additional means of cooling and microwave absorption while permitting independent control of cooling fluid within cooling lumens 232A, 232B, and 234A, 234B. However, since cooling balloon 240 and cooling inflation lumen 230 do not permit recirculation of fluid within cooling balloon 240 while inflated, fluid within cooling exhaust lumens 234A, 234B are relied upon to carry heat away from cooling fluid within cooling balloon 240 via thermal conduction.

Although the present invention has been described with reference to preferred embodiments, workers skilled in the art will recognize that changes may be made in form and detail without departing from the spirit and scope of the invention.

What is claimed is:

1. A method for treating a diseased portion of cardiac tissue comprising:

inserting an intravascular catheter into a cardiovascular system including a microwave antenna disposed within an antenna lumen, a plurality of fluid flow lumens substantially surrounding the antenna lumen and a balloon having an inflatable portion which partially surrounds the antenna lumen, the balloon being in communication with the fluid flow lumens;

advancing the catheter through the cardiovascular system with the balloon in a deflated state until a distal end of the catheter is within a ventricle of a heart and adjacent a diseased portion of cardiac tissue spaced from a wall of the ventricle;

positioning the distal end of the catheter so that a first side of the catheter is immediately adjacent the diseased portion to be treated and a second side of the catheter is adjacent blood within the ventricle;

cooling the ventricle by directing cooling fluid to flow through the fluid flow lumens to cool a surface of the ventricle wall adjacent the catheter first side and directing cooling fluid to flow through the balloon and the fluid flow lumens to cool blood within the ventricle adjacent the catheter second side; and heating the diseased portion of tissue spaced from a surface of the ventricle wall with microwave energy from the microwave antenna at a power range and for a time sufficient to necrose the diseased portion of tissue.

2. A method for treating ventricular tachycardia comprising:

inserting an intravascular catheter into a vascular system including a microwave antenna disposed within an antenna lumen, a pair of fluid flow lumens surrounding the antenna lumen and a balloon having an inflatable portion which partially surrounds the antenna lumen and which is in fluid communication with the fluid flow lumens and having an inflated and deflated state;

advancing the intravascular catheter through the vascular system with the cooling balloon in its deflated state until a distal end of the catheter is within a chamber of a heart adjacent a wall of the chamber;

positioning the catheter so that a first side of the intravascular catheter is immediately adjacent the chamber wall and a second side of the intravascular catheter is exposed to blood within the chamber; and heating a portion of tissue beyond a surface of the chamber wall with microwave energy from the microwave antenna at a power range and for a time sufficient to necrose the tissue portion while delivering cooling fluid through the fluid flow lumens to cool the chamber wall surface adjacent the intravascular catheter first side and through the balloon to cool the blood within the chamber.

3. The method of claim 2 wherein the balloon of the intravascular catheter has a generally arc-shaped transverse cross-section and is immediately adjacent the fluid flow lumens on the second side of the intravascular catheter shaft.

4. The method of claim 3 and further comprising:

inserting a guide catheter within the vascular system prior to inserting the intravascular catheter and advancing the guide catheter therethrough until a distal end of the guide catheter is within a chamber of the heart adjacent the chamber wall and a proximal end of the guide catheter extends proximally outside a patient; and inserting the intravascular catheter within a proximal end of the guide catheter with the balloon in its deflated state and advancing the intravascular catheter therethrough until the distal end of the intravascular catheter is adjacent the wall of the chamber.

5. The method of claim 4 and further comprising:

delivering fluid through the fluid flow lumens and into the balloon at a pressure sufficient to inflate the balloon and maintain the balloon in its inflated state after the first side of the intravascular catheter is positioned adjacent the surface of the chamber wall.

6. An intravascular catheter for microwave thermal therapy comprising:

an elongate shaft having a first end, a second end, an outer surface and a plurality of lumens which extend between the first end and the second end of the shaft, the plurality of lumens including:

an antenna lumen; and a plurality of fluid flow lumens arranged about the antenna lumen; and a balloon connected to the outer surface of the elongate shaft along a portion of the shaft, the balloon having an inflatable portion which partially surrounds the antenna lumen and which is in fluid communication with at least one of the plurality of fluid flow lumens.

7. The intravascular catheter of claim 6 wherein the plurality of fluid flow lumens further comprises a first and second pair of fluid flow lumens and the inflatable portion of the balloon is disposed adjacent the second pair of fluid flow lumens.

8. The intravascular catheter of claim 7 wherein an inner wall of the inflatable portion of the balloon is common with a wall defining an outer wall of the second pair of fluid flow lumens so that a majority of the inflatable portion of the balloon is immediately adjacent the second pair of fluid flow lumens.

9. The intravascular catheter of claim 6 further comprising an electromagnetic radiation antenna within a portion of the antenna lumen of the shaft, the portion of the antenna lumen being adjacent to the balloon.

10. The intravascular catheter of claim 9 wherein the balloon has a length greater than a length of the portion of the antenna lumen which contains the antenna.

11. An intravascular catheter for microwave therapy comprising:

an elongate shaft having a first end, a second end, an outer surface and a plurality of lumens which extend between the first end and the second end of the shaft, the plurality of lumens including:

an antenna lumen;

a plurality of fluid flow lumens arranged about the antenna lumen; and an inflation lumen; and a balloon connected to the outer surface of the elongate shaft along a portion of the shaft, the balloon having an inflatable portion which partially surrounds the antenna lumen and which is in fluid communication with the inflation lumen.

12. A device for treatment of ventricular tachycardia comprising:

an intravascular catheter adapted to be inserted into a ventricle of the heart, the catheter having an outer surface, a first end, a second end, a first side for orientation toward a wall of the ventricle, and a second side for orientation toward blood within the ventricle;

radiating means within the catheter for producing an emission capable of necrosing target cardiac tissue beyond a surface of the wall of the ventricle;

means within the catheter disposed between the radiating means and the outer surface of the catheter on both the first side and the second side of the catheter for preventing necrosis of the surface of the ventricle wall; and a balloon positioned along a portion of the catheter adjacent to the radiating means, the balloon being connected to the outer surface of the catheter and having an inflatable portion on the second side of the catheter in fluid communication with the means for preventing necrosis of the surface of the ventricle wall.

13. An intravascular catheter for microwave therapy comprising:

an elongate shaft having a first end, a second end, an outer surface, and a plurality of lumens extending between the first end and the second end, the plurality of lumens including:
an antenna lumen; and
a first fluid flow lumen and a second fluid flow lumen arranged in a side by side relationship and partially surrounding the antenna lumen; and a balloon connected to the outer surface of the elongate shaft along a portion of the shaft, the balloon having an inflatable portion which partially surrounds the antenna lumen and which is in fluid communication with the second fluid flow lumen.

14. The catheter of claim 13 wherein an inner wall of the inflatable portion of the balloon is common with a wall defining an outer wall of the second fluid flow lumen so that a majority of the inflatable portion of the balloon is immediately adjacent the second fluid flow lumen.

15. A device for treatment of ventricular tachycardia comprising:

an intravascular catheter adapted to be inserted into a ventricle of a heart, the catheter having an outer surface, a first end, a second end, a first side for orientation toward a wall of the ventricle, and a second side for orientation toward blood within the ventricle;

radiating means within the catheter for producing an emission capable of necrosing target cardiac tissue spaced from a surface of the wall of the ventricle;

first fluid circulation means within the catheter adjacent to the radiating means on both the first side and the second side of the catheter for protecting the surface of the ventricle wall; and second fluid circulation means on the catheter along the second side of the catheter adjacent to the radiating means for cooling the blood within the ventricle.

16. The device of claim 15 wherein the intravascular catheter further comprises:

an inflation lumen for supplying a cooling fluid to the second fluid circulation means.

17. A device for treatment of ventricular tachycardia comprising:

an intravascular catheter adapted to be inserted into a ventricle of a heart, the catheter having an outer surface, a first end, a second end, a first side for orientation toward a wall of the ventricle, and a second side for orientation toward blood within the ventricle;

radiating means within the catheter for producing a microwave emission capable of necrosing target cardiac tissue spaced from a surface of the wall of the ventricle;

first cooling means within the catheter disposed between the radiating means and the outer surface of the catheter on the first side of the catheter for cooling the ventricle wall and for absorbing a first amount of the microwave emission; and second cooling means disposed around the radiating means on the second side of the catheter for absorbing a second amount of the microwave emission from the radiating means and for cooling blood within the ventricle, the second cooling means having an inner portion and an outer portion adjacent the inner portion.

18. The device of claim 17 wherein the intravascular catheter further comprises:

an inflation lumen for supplying a cooling fluid to the outer portion of the second cooling means.

19. A device for treatment of ventricular tachycardia comprising:

an intravascular catheter adapted to be inserted into a ventricle of a heart, the catheter having an outer surface, a first end, a second end, a first circumferential portion for orientation toward a wall of the ventricle, and a second circumferential portion for orientation toward blood within the ventricle;

radiation means within the catheter for producing an emission capable of necrosing target cardiac tissue spaced from a surface of the wall of the ventricle;

first means within the catheter adjacent to the radiation means for preventing necrosis of the surface of the ventricle wall; and a balloon connected to the outer surface of the catheter adjacent to the radiation means, the balloon being configured to inflate on the second circumferential portion of the catheter.

20. A device for treatment of ventricular tachycardia comprising:

an intravascular catheter adapted to be inserted into a ventricle of a heart, the catheter having an outer surface, a first end, a second end, a first circumferential portion for orientation toward a wall of the ventricle, and a second circumferential portion for orientation toward blood within the ventricle;

radiation means within the catheter for producing an emission capable of necrosing target cardiac tissue spaced from a surface of the wall of the ventricle;

first means within the catheter disposed between the radiating means and the outer surface of the catheter at both the first and second circumferential portions for preventing necrosis of the surface of the ventricle wall; and a balloon connected to the outer surface of the catheter adjacent to the radiation means, the balloon defining a chamber on the second circumferential portion of the catheter.

* * * * *

UNITED STATES PATENT AND TRADEMARK OFFICE
CERTIFICATE OF CORRECTION

PATENT NO. : 5,861,021
DATED : JANUARY 19, 1999
INVENTOR(S) : SCOTT P. THOME ET AL.

It is certified that error appears in the above-identified patent and that said Letters Patent is hereby corrected as shown below:

On the Title Page, under [73] Assignee: insert --Urologix, Inc., Minneapolis, MN.--

Col. 4, line 32, delete "0.2", insert --2--

Signed and Sealed this

Twenty-sixth Day of October, 1999

Attest:

Q. TODD DICKINSON

*Attesting Officer*      *Acting Commissioner of Patents and Trademarks*